(12) United States Patent
Boachie-Adjei et al.

(10) Patent No.: US 8,672,944 B2
(45) Date of Patent: Mar. 18, 2014

(54) SYSTEM AND METHOD FOR PERFORMING SPINAL SURGERY

(75) Inventors: Oheneba Boachie-Adjei, Briarcliff, NY (US); Andrew Thomas Rock, Spring Grove, PA (US); Raymund Woo, Orlando, FL (US); Michael Barrus, Ashburn, VA (US); Scott Jones, Mcmurray, PA (US)

(73) Assignee: K2M, Inc., Leesburg, VA (US)

( * ) Notice: Subject to any disclaimer, the term of this patent is extended or adjusted under 35 U.S.C. 154(b) by 320 days.

(21) Appl. No.: 13/000,639

(22) PCT Filed: Jun. 29, 2009

(86) PCT No.: PCT/US2009/049064
§ 371 (c)(1),
(2), (4) Date: Mar. 15, 2011

(87) PCT Pub. No.: WO2009/158707
PCT Pub. Date: Dec. 30, 2009

(65) Prior Publication Data
US 2011/0172714 A1 Jul. 14, 2011

Related U.S. Application Data

(60) Provisional application No. 61/133,357, filed on Jun. 27, 2008, provisional application No. 61/104,411, filed on Oct. 10, 2008.

(51) Int. Cl.
*A61B 17/88* (2006.01)
(52) U.S. Cl.
USPC ........... 606/86 A; 606/246; 606/279; 606/914

(58) Field of Classification Search
USPC ................. 606/90, 104, 105, 914, 916, 279
See application file for complete search history.

(56) References Cited

U.S. PATENT DOCUMENTS

| | | | |
|---|---|---|---|
| 5,720,751 A | 2/1998 | Jackson | |
| 6,123,707 A | 9/2000 | Wagner | |
| 6,235,028 B1 * | 5/2001 | Brumfield et al. | 606/53 |
| 6,957,758 B2 | 10/2005 | Aranyi | |
| 7,220,262 B1 * | 5/2007 | Hynes | 606/279 |
| 7,776,072 B2 * | 8/2010 | Barry | 606/265 |
| 7,951,175 B2 * | 5/2011 | Chao et al. | 606/279 |
| 8,221,426 B2 * | 7/2012 | Justis et al. | 606/86 A |
| 2002/0052603 A1 | 5/2002 | Nichols et al. | |
| 2004/0267275 A1 | 12/2004 | Cournoyer et al. | |

(Continued)

OTHER PUBLICATIONS

International Search Report and Written Opinion issued by the U.S. Searching Authority in counterpart PCT Application No. PCT/US2009/49064, completed Aug. 14, 2009; mailed Aug. 25, 2009; 8 pages.

*Primary Examiner* — Jerry Cumberledge
(74) *Attorney, Agent, or Firm* — Carter, DeLuca, Farrell & Schmidt, LLP

(57) ABSTRACT

Systems and methods for surgical spinal correction are disclosed. A system including a plurality of bone screws, spinal rods, manipulators, and/or transverse couplers is disclosed for the manipulation of the spinal column is disclosed. A method of achieving, in a single action, manipulation and/or rotation of the spinal column using the disclosed system is disclosed. Also disclosed is a method of conducting spinal surgery to correct spinal deformities wherein spinal rods are pre-bent in a physiological sagittal plane prior to attachment of the vertebrae using bone screws.

16 Claims, 24 Drawing Sheets

(56) References Cited

U.S. PATENT DOCUMENTS

| | | |
|---|---|---|
| 2005/0192579 A1* | 9/2005 | Jackson .................... 606/72 |
| 2005/0277927 A1* | 12/2005 | Guenther et al. .............. 606/61 |
| 2006/0025769 A1 | 2/2006 | Dick et al. |
| 2006/0200132 A1* | 9/2006 | Chao et al. ................... 606/61 |
| 2006/0271050 A1* | 11/2006 | Piza Vallespir ............... 606/61 |
| 2007/0093817 A1 | 4/2007 | Barrus et al. |
| 2007/0213715 A1* | 9/2007 | Bridwell et al. ............... 606/61 |
| 2007/0213716 A1* | 9/2007 | Lenke et al. .................. 606/61 |
| 2007/0270811 A1 | 11/2007 | Dewey |
| 2007/0270867 A1 | 11/2007 | Miller et al. |
| 2007/0282337 A1 | 12/2007 | Garamszegi |
| 2008/0015601 A1 | 1/2008 | Castro et al. |

* cited by examiner

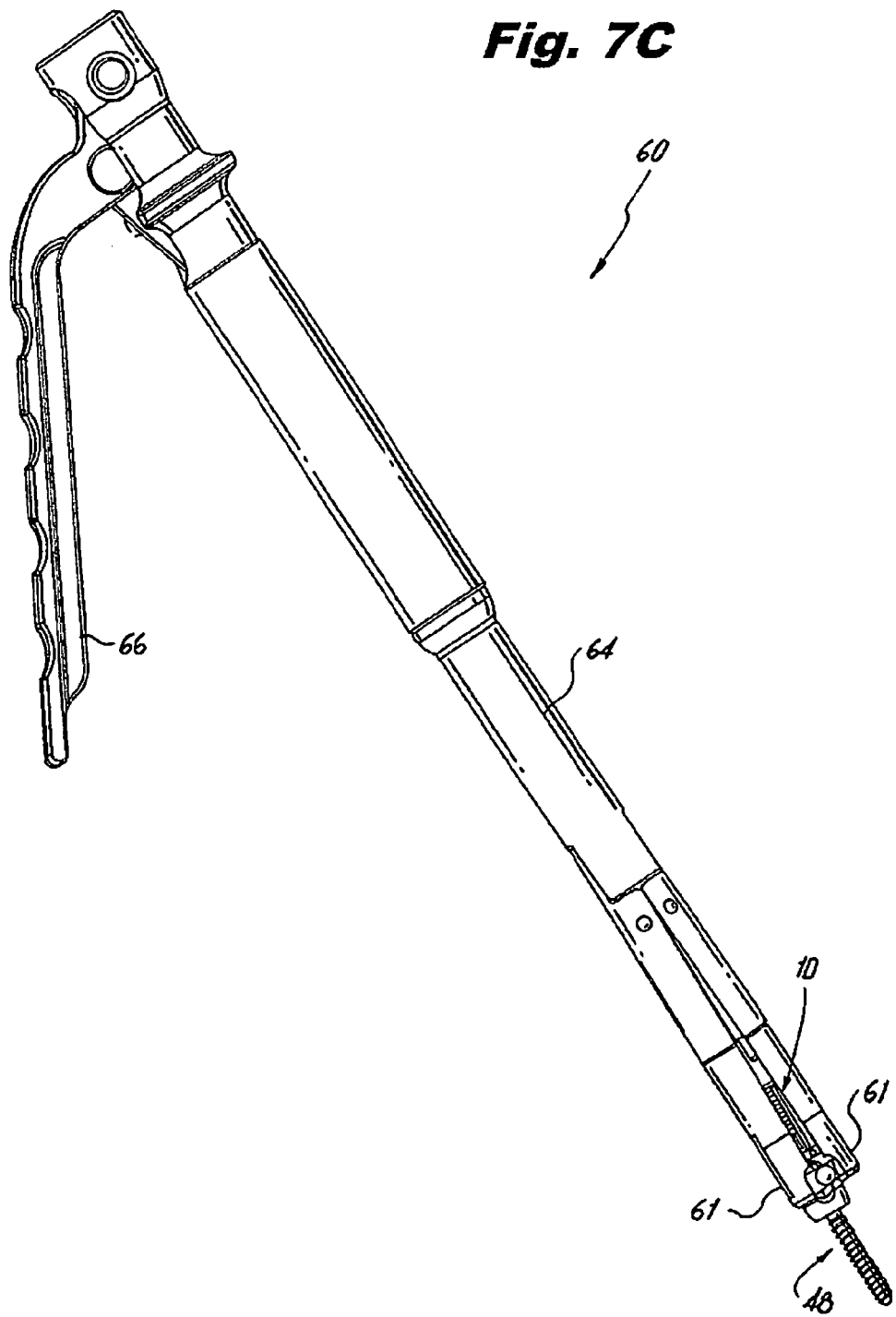

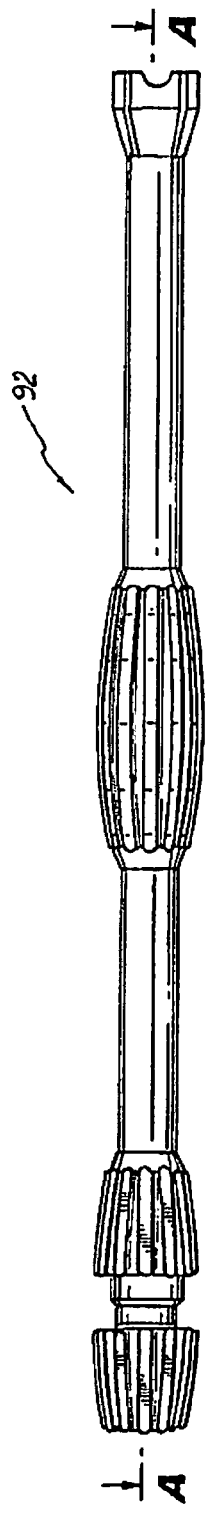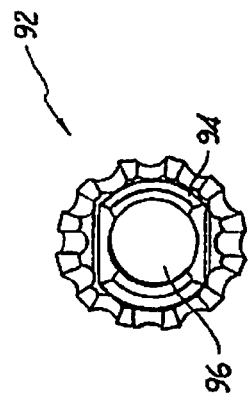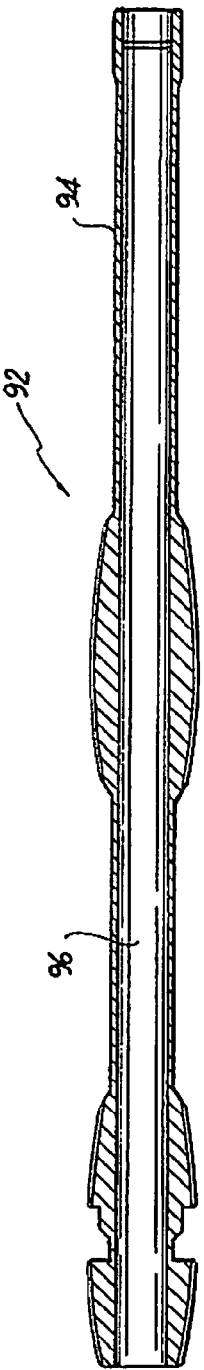
Fig. 15
Fig. 15A
Fig. 16

SYSTEM AND METHOD FOR PERFORMING SPINAL SURGERY

CROSS-REFERENCE TO RELATED APPLICATIONS

The present application is a National Stage Entry of PCT/US2009/049064, which was filed Jun. 29, 2009, and claims the benefit of U.S. Provisional Patent Application Ser. No. 61/104,411 filed Oct. 10, 2008, and U.S. Provisional Application Ser. No. 61/133,357 filed Jun. 27, 2008. The entire contents of each of these prior applications are incorporated by reference herein.

BACKGROUND

1. Technical Field

The present disclosure relates to orthopedic surgery, and more particularly, to apparatuses and methods for surgical correction of spinal deformities.

2. Background of Related Art

Correction of a spinal deformity typically requires stabilization and fixation of vertebrae in a particular spatial relationship. Surgical spinal correction procedures involve the placement of a plurality of bone pins, anchors, cables, hooks, or screws placed in adjacent vertebrae and using spinal rods to maintain a predetermined spatial relationship between the vertebrae. Such devices may be permanently implanted in the subject. However, in other cases, the devices may subsequently be removed when no longer needed.

Certain deformities of the spinal column require considerable correction, e.g., severe scoliosis of the spine. The use of conventional devices for spinal correction may necessitate a series of separate surgeries. For example, scoliosis treatment typically involves the use of rigid screw and connecting rods. Such connections fail to provide any degree of flexibility during the surgical procedure, thereby inhibiting manipulation and repositioning of the spinal vertebrae prior to locking the connecting rods into a rigid connection with the bone screws.

To ease the introduction and locking of connecting rods when building a spinal construct, polyaxial bone screws have been employed. However, polyaxial bone screws and other flexible connections may provide a range of motion that is too great in cases such as scoliosis. It may be necessary to restrict the range of motion during the spinal column manipulation process to only uniplanar or monoaxial movement of the connecting rod relative to the bone screw. Achieving proper alignment using conventional connecting rod and screw systems that fail to limit movement of a bone screw's head to a single plane or single axis of rotation may be problematic. While a rigid bone screw may facilitate spinal manipulation, attachment of the connecting rods is more difficult using such devices. Avoiding unwanted multi-axial movement of a screw head during manipulation while facilitating attachment of a connecting rod can be achieved by utilizing uniplanar or monoaxial screw heads.

Conventional surgical methods, however, are not designed to take full advantage of the employment of specialized bone screws, such as uniplanar and monoaxial bone screws. For example, many bone screws utilize a set screw or locking nut design to secure the rod to the screw. Such a locking system does not facilitate partial locking of the screw to the rod so that the relative position of the rod and the screw will remain stabile as adjustments are made to the position of that screw and other screws along the rod prior to final locking, and throughout final locking of the construct.

SUMMARY

Spinal methods and systems are disclosed herein for the surgical correction of spinal deformities involving the manipulation of spinal rods into position relative to the spinal column and locking bone screws, e.g., polyaxial, uniplanar, and/or monoaxial taper lock screws, to the spinal rods. It is contemplated that at least some of the polyaxial screws may be setscrew style screws. The disclosed methods may employ a combination of taper lock screws in one portion of the construct and setscrew or nut style screws in another portion of the construct. Spinal rods that are pre-bent in a physiological sagittal plane may be used.

A kit providing instruments for use in the methods described herein is also disclosed. The kit includes a plurality of spinal rods, rod reduction devices that include a screwjack mechanism, and manipulators.

In any of the disclosed systems or methods, the spinal rods may be pre-bent in a physiological sagittal plane prior to attachment of the vertebrae using bone screws. A rod reduction device having taper lock screw connecting mechanisms and a rod reduction screw jack mechanism can be used to facilitate rod reduction and spinal rotation corrections in a single step. The screw jack mechanism rod reduction devices may be attached to bone screws on the concave side of the deformity and manipulators may be attached to bone screws on the convex side of the deformity to facilitate rod reduction and spinal rotation in a single action. In general, the disclosed methods include the steps of implanting a plurality of bone screws into multiple bores of the spine using taper lock bone screws, and more particularly utilizing multiplanar taper lock screws including, inter alfa, multiplanar taper lock screws, uniaxial taper lock screws, and monomial taper lock screws. Taper lock screws provide the ability to partially lock the screw, permitting further or continued manipulation of the spine while holding position while partially locked prior to fully locking. Prior to connecting the spinal rods, the spinal column may be manually manipulated to reduce the deformity.

Reduction jacks may be mounted on at least some of the plurality of bone screws and a rod is inserted between the rod reduction jacks and the bone screws. The rod reduction jacks may be partially actuated in an alternating or sequential manner to gradually reduce the rod to each screw. Depending upon the type of spinal deformity, rod reduction may be performed first on one side of the deformity followed by rod reduction on the other side of the deformity. Alternatively, the rod reduction steps may be performed on bilaterally on both sides of the deformity.

To facilitate sagittal alignment of the spinal rods, correction including compression, distraction, and/or derotation may be performed with the screws implanted in the vertebral body and partially locked. Partial actuation of the rod reduction jacks to each bone screw may be achieved by mounting a partial screw locking instrument over the rod reduction jack and bone screw and partially locking the bone screw with the rod reduction jack in place.

Taper lock screws may used in one portion of the spinal construct and set screw or nut style screws are used in another portion of the spinal construct. Also, in an embodiment of a method for conducting spinal surgery, a portion of a spinal rod is anchored to vertebrae on the spinal column using polyaxial screws while the remaining portion of the spinal rod is anchored to the vertebrae using uniplanar taper lock bone screws with the lowest instrumented vertebra (LIV) anchored to the spinal rods using monoaxial bone screws. Countertorsion of the lowest instrumented vertebra may be accomplished. For example, a linked transverse coupler attached to the lowest instrumented vertebra will facilitate stabilization and provide counter torsion during correction.

Alignment tubes or similar instruments may be mounted over one or more of the reduction jacks and used to manipulate the spine into a desired, corrected position. Once positioned, the alignment tubes may be removed and a partial screw locking instrument may be mounted over the rod reduction jack and screw and the screw may be partially locked with the rod reduction jack in place. The partial screw locking instrument and the rod reduction jack may be removed from each screw. A screw locking instrument may be used to fully lock each screw. Some of the screws may be locked completely, while others may be partially locked, thereby allowing additional adjustments to be made.

Also disclosed herein is a system for repositioning vertebrae to correct a spinal deformity including a first rod reduction device coupled to a first vertebral body of a spinal column, a second rod reduction device coupled to a second vertebral body of a spinal column, a first manipulator coupled to the first rod reduction device, a second manipulator coupled to the second rod reduction device, and a coupler coupling the first and second manipulators.

In another embodiment, the system for repositioning vertebrae of a spinal column may include a first assembly including a first rod reduction device and a second rod reduction device, the first and second rod reduction devices coupled to a first vertebral body of a spinal column, wherein a first manipulator is coupled to the first rod reduction device and a second manipulator is coupled to the second rod reduction device, a second assembly including a third rod reduction device and a fourth rod reduction device, the third and fourth rod reduction devices coupled to a second vertebral body of the spinal column, wherein a third manipulator is coupled to the third rod reduction device and a fourth manipulator is coupled to the fourth reduction device, and a coupler coupling the first and second assemblies.

The system may include a first assembly including first and second manipulators, each manipulator coupled to a different pedicle of a first vertebral body and a first transverse coupler coupling the first and second manipulators, a second assembly including third and fourth manipulators, each manipulator coupled to a different pedicle of a second vertebral body and a second transverse coupler coupling the third and fourth manipulators, and a coupler configured and adapted to exert force on the first and second assemblies.

In any of these embodiments, the coupler may be configured and adapted for a practitioner to grasp and apply pressure thereon to reposition the vertebral bodies relative to each other. In another embodiment, a handle may be configured and adapted to engage one or more of the manipulators at proximal ends thereof.

Transverse couplers may couple manipulators on either side of the spinal deformity. For example, in an embodiment, a first transverse coupler couples the first and second manipulators and a second transverse coupler couples the third and fourth manipulators and the coupler includes a grip configured and adapted to capture the first and second transverse couplers therein. The transverse coupler may be configured and adapted for a practitioner to grasp and apply pressure thereon to reposition the vertebral body.

The transverse coupler may include a first arm portion including a first ring and a second arm portion including a second ring, in which the first and second arm portions are coupled to each other and the first and second rings are each configured and adapted to receive a portion of one of the control knobs therein. The first and second rings may each include a sleeve slidably disposed therein that is configured and adapted to releasably receive a portion of one of the control knobs therein.

A coupling device that is configured and adapted to couple at least two transverse couplers may be used. In an embodiment, the coupling device may include a grip that is configured and adapted to capture one or more transverse couplers therein. The grip may include a first and a second arm that are pivotably coupled to each other.

Alternatively, the coupling device may include a bar having a longitudinal axis and including a pair of graspers, each grasper being configured and adapted to engage an arm portion of the transverse coupler. Each grasper may be repositionable along the longitudinal axis. A knob may be disposed along a surface of the bar, e.g., centrally disposed along an upper surface of the bar, to facilitate manipulation of the coupling device by a practitioner.

The various embodiments of the present disclosure will be more readily understood from the following detailed description when read in conjunction with the appended figures.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 7C is a perspective view of the screw locking device of FIG. 7a shown coupled to one of the plurality of rod reduction devices of FIG. 3 and one of the plurality of bone screws of FIG. 3;

FIG. 15 is a front view of an alignment tube accessory;

FIG. 15A is a side view of the alignment tube accessory of FIG. 15;

FIG. 16 is a cross-sectional view along section line A-A of the alignment tube accessory of FIG. 15;

DETAILED DESCRIPTION OF THE EMBODIMENTS

Figure 1A:
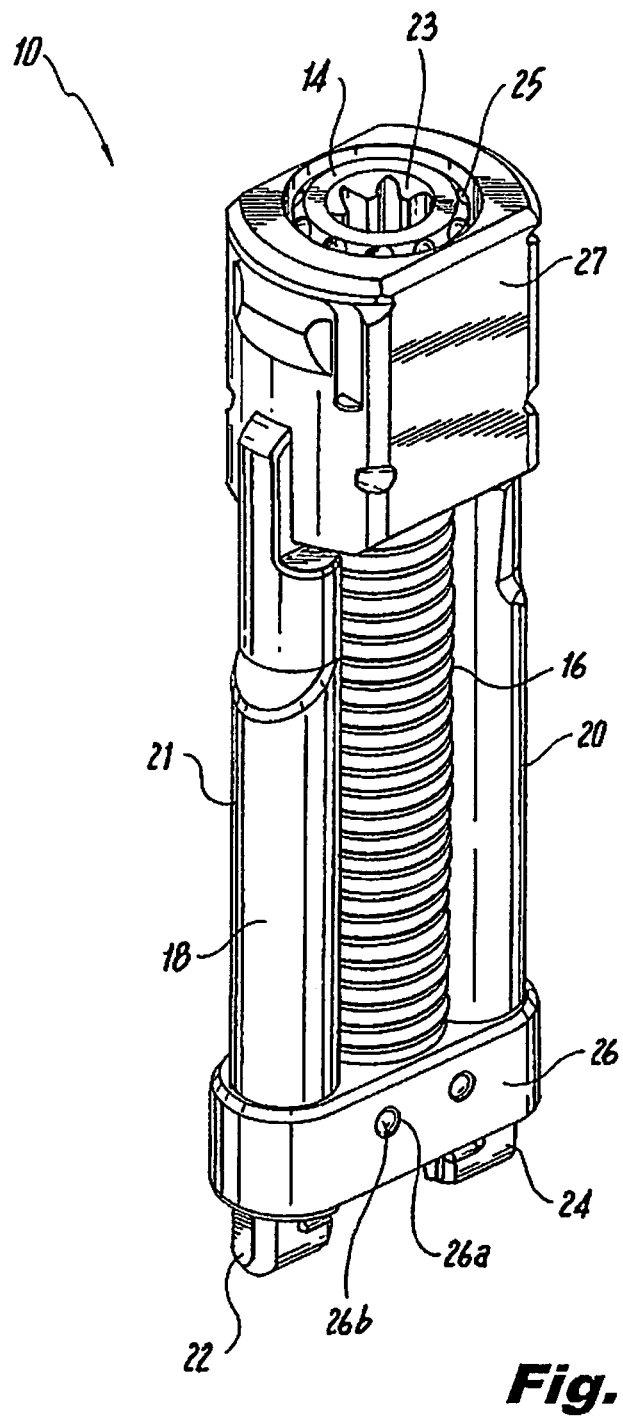
FIG. 1A is a perspective view of a rod reduction device having a screw jack mechanism in a closed position configured for connection to a head of a bone screw.

Embodiments of the presently disclosed apparatuses and methods for spinal surgery will now be described in detail with reference to the appended drawings, in which like reference numerals designate identical or corresponding elements in each of the several views. Throughout the following description, the term "proximal," will refer to the end of a device or system that is closest to the operator, while the term "distal" will refer to the end of the device or system that is farthest from the operator. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, i.e., away from the middle of the body of the patient. The term "posterior" indicates a direction toward the patient's back, while the term "anterior" indicates a direction toward the patient's front.

A rod reduction device 10 will now be described with reference to FIGS. 1A and 1D. The rod reduction device 10 is described in U.S. Patent Application Publication 2009/0018593, the entire contents of which, is hereby incorporated by reference. In particular, the rod reduction device 10 includes a jack mechanism 12 movably engaged with an elongated grasping fork assembly 21 that includes a fork assembly body 27. The elongated grasping fork assembly 21 includes a fork assembly body 27 that defines a body through passage 75 that is sized and complimentary configured to permit passage of the elongated screw shaft 16 of the screw jack mechanism 12. An upper portion 73 of the body through passage 75 is provided with complimentary threads to the threads of the elongated threaded screw shaft 16.

Figure 1B:
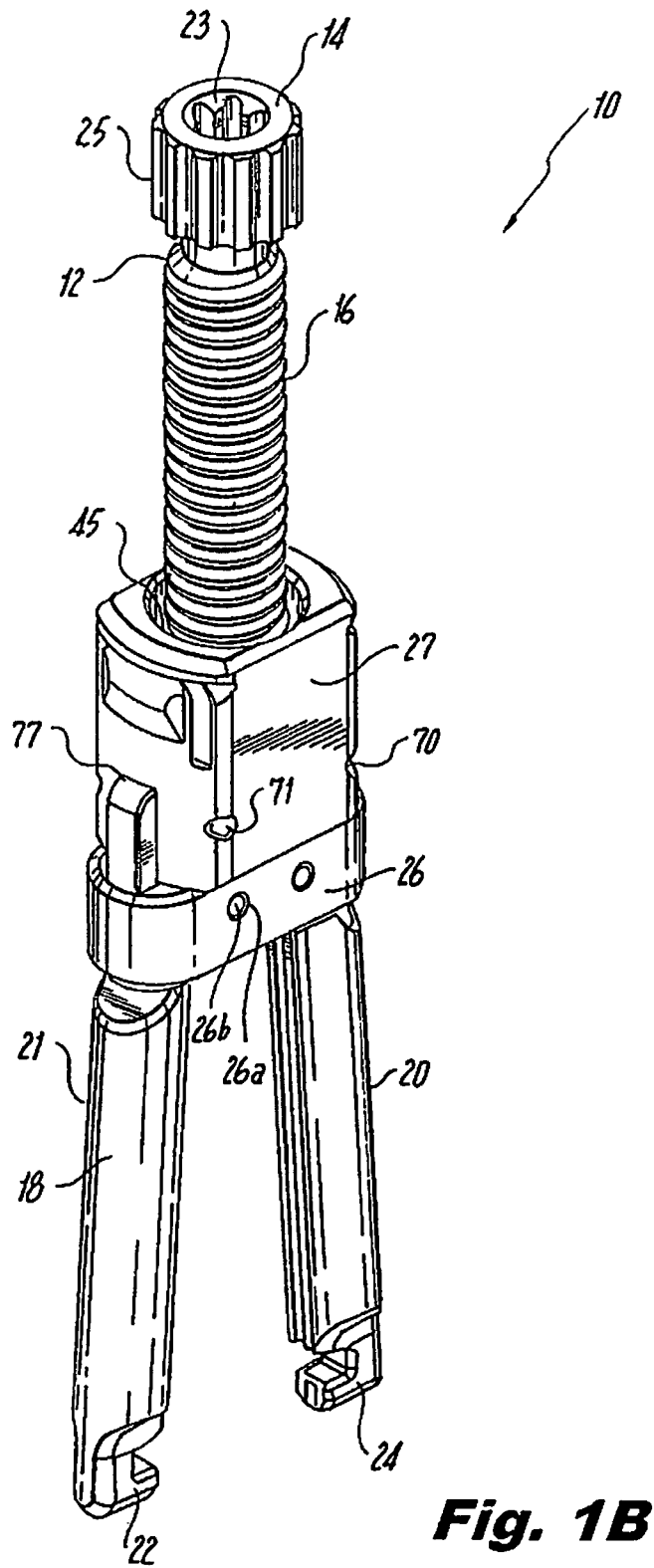
FIG. 1B is a perspective view of the rod reduction device of FIG. 1 with the screw jack mechanism in an open position.
Figure 1C:
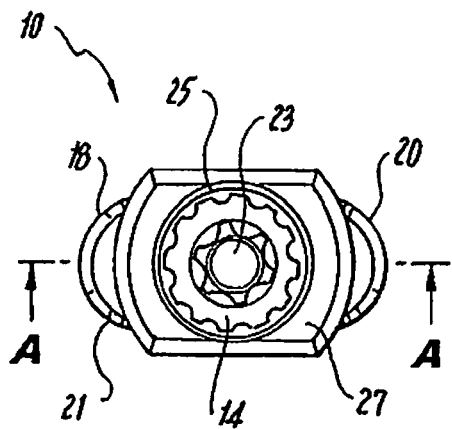
FIG. 1C is a top view of the rod reduction device of FIG. 1.
Figure 1D:
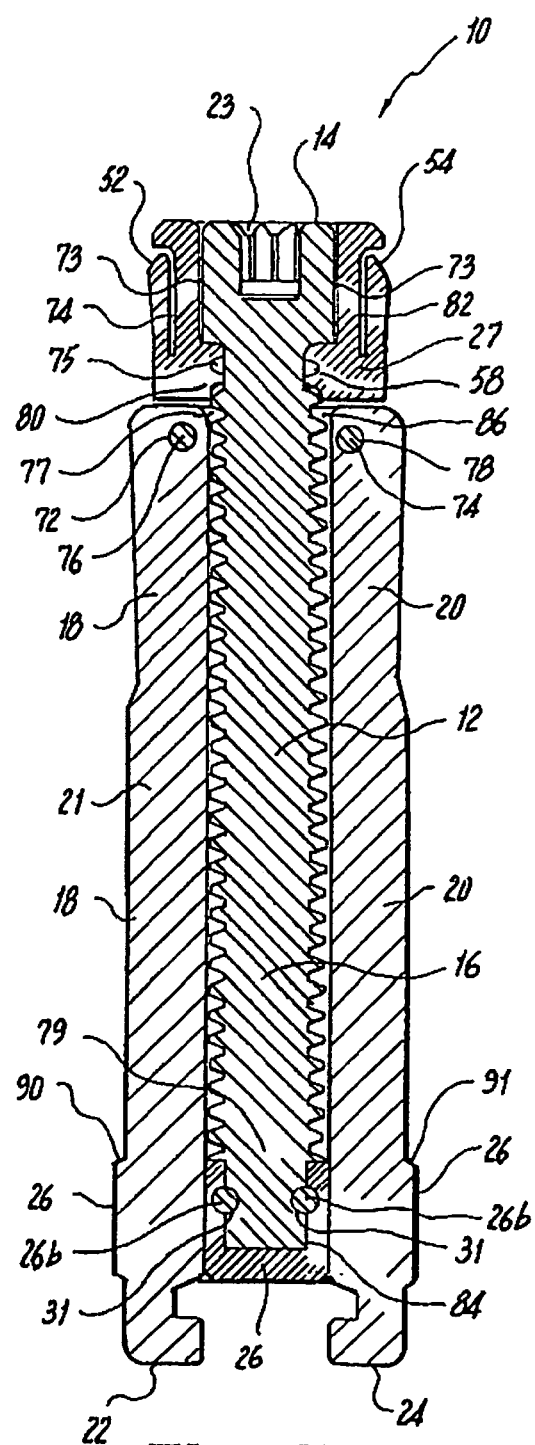
FIG. 1D is a cross sectional view along section line A-A of FIG. 1.

As shown best in FIG. 1D, a first and a second compression slot 74, 82 are defined on opposing sides of the fork assembly body 27. Outer most from the compression slots 74, 82 are associated first and second accessory tabs 52, 54, which extend proximally from inferior portions 80, 58 of the fork assembly body 27. The first and second accessory connection tabs 52, 54 are provided to facilitate a positive engagement with other instruments or accessories that can be used in combination with the rod reduction device 10, such as, for example an alignment tube, generally shown as 92 in FIGS. 15 and 16. The exemplary embodiment of the alignment tube 92 is provided as a trocar-like device sized and configured to be circumferentially disposed around the device 10 and to be useful in the positioning of the device 10 in a patient. The accessory connection tabs 52, 54 extending outward from the fork assembly body 27 of device 10 can make sufficient contact with the inner wall 94 of the lumen 96 of the alignment tube 92 so as to facilitate movement of the device 10 into a proper position over the head of a bone screw into which a rod is to be placed. The alignment tube 92 can be provided with additional lumens or accessories to improve its usefulness in facilitating the positioning of device 10 over the bone screw during a surgical procedure.

The screwjack mechanism 12 includes an elongated screw shaft 16 that terminates at its most proximal end with a controlling member 14 and terminates at its most distal end with a rod contact member or anvil 26. The rod contact member or anvil 26 is attached to the distal end of the threaded screw shaft 16 and is positioned in sliding circumferential contact with a pair of elongated grasping members 18, 20. Each of the grasping members 18, 20 include an inwardly directed screw grasping element 22, 24 at a distal end thereof. As seen in FIGS. 1A and 1B, the rod contact member 26 is connected to the distal end of the threaded screw shaft 16 by contact member retention pins 26b that pass through retention pin holes 26a defined in the rod contact member 26 at a position that permits the retention pins 26b to also rest within a retention pin groove 31 that is circumferentially defined in a lower most portion 79 of the threaded screw shaft 16. The lower most portion 79 of the threaded shaft 16 is not threaded but rather is configured to have a smooth surface that can facilitate free rotational movement of that portion of the shaft 16 within an appropriately sized and configured contact member shaft well 84 and is then rotationally retained therein by the insertion of the contact member retention pins 26b. The contact member shaft well 84 is sized and configured to receive the smooth surfaced lower most portion 79 of the distal end of the threaded shaft 16 and to allow free rotational movement of that lower most portion 79.

As shown in FIG. 1D, the rod contact member 26 defines, at a first and a second opposing end of the rod contact member 26, a first and a second through passage 90, 91. The first and second through passage 90, 91 are sized and configured to facilitate engagement of the elongated grasping fork assembly 21 with the screw jack mechanism 12 of the rod reduction device 10.

Figure 17:
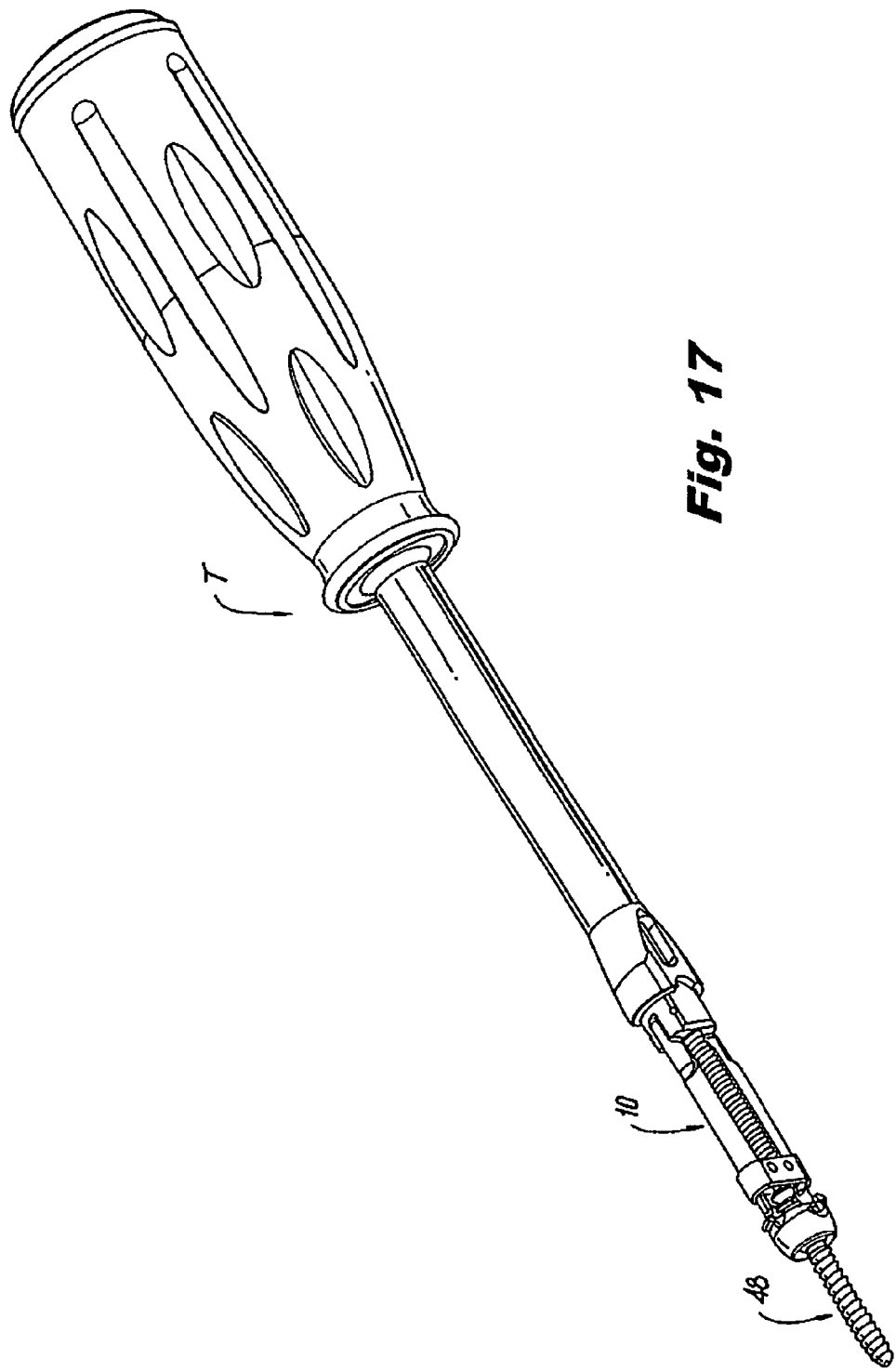
FIG. 17 is an isometric view of a driving instrument assembled to the rod reduction device of FIG. 1A and a bone screw.

Rotation of the controlling member 14 in one direction may be achieved either by hand or with a tool T, e.g., a screwdriver type device, as shown in FIG. 17. The controlling member 14 includes circumferentially disposed gripping contacts 25, which facilitate a user's manual or instrumental grip on the controlling member 14 during use. In addition, a tool engagement recess 23 can be configured to complement the shape of a tightening or loosening tool to facilitate rotational movement of the controlling member 14 of the screw shaft 16. The connection tabs 52, 54 when manually compressed inward effect an outward bias of the inferior portions 80, 58 of the fork body assembly 27 so as to slightly relieve pressure on the threaded portion of the body through passage 75 from the threadably engaged threaded screw shaft 16 of the screw jack mechanism 12 to provide some relief of inward pressure during rotation of the controlling member 14 and the screw shaft 16 and conversely, when no pressure is applied to the accessory connection tabs 52, 54, the inward bias of the threaded portion of the body 75 serves to hold the threaded shaft 16 in place to provide a selectively releasable position securing effect.

Figure 3:
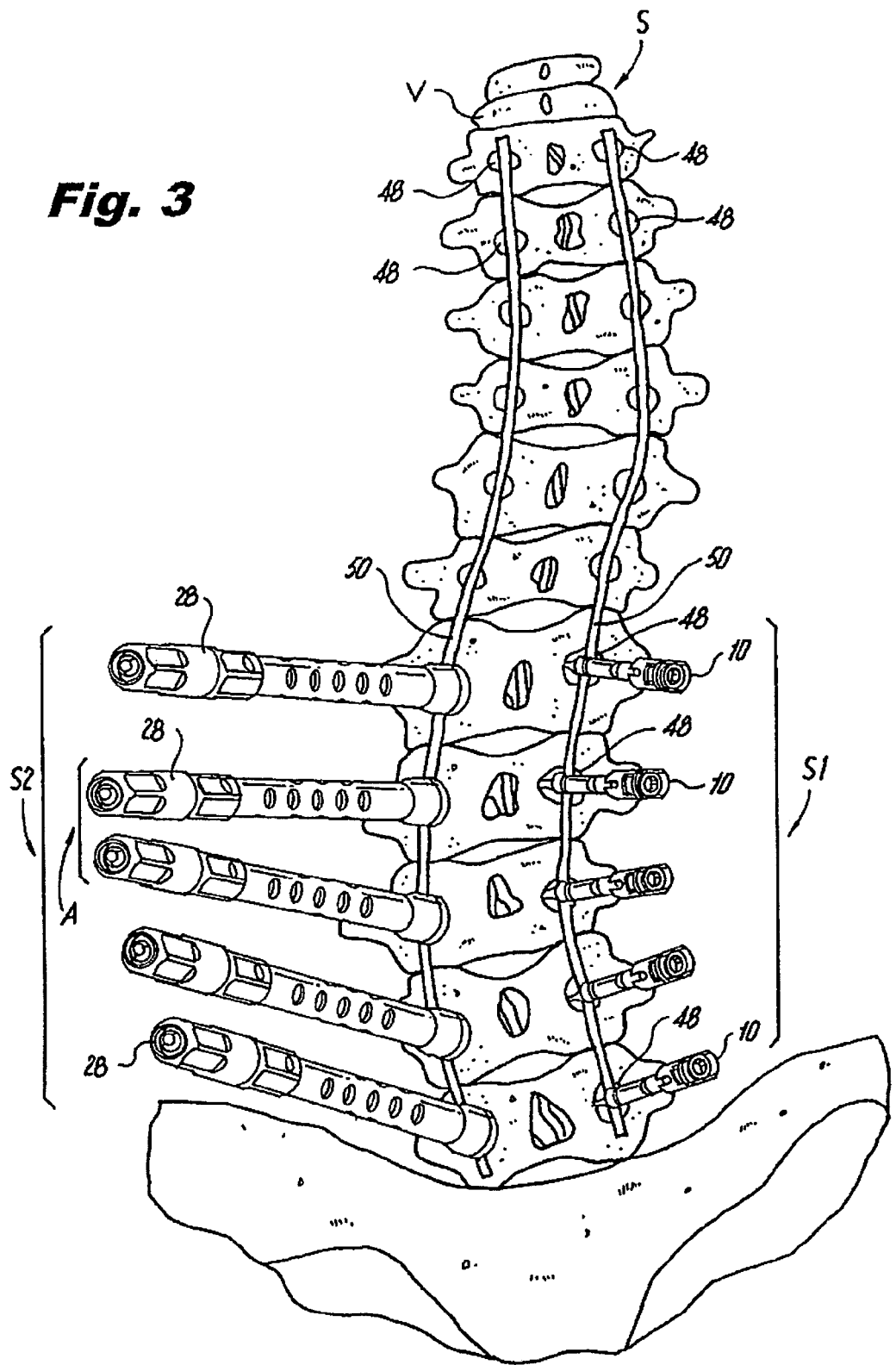
FIG. 3 shows a dorsal view of a section of a spinal column with a plurality of bone screws attached to spinal vertebrae of the spinal column, two spinal rods engaged with the plurality of bone screws, a plurality of rod reduction devices attached to the bone screws, and a plurality of manipulators attached to the bone screws.
Figure 5A:
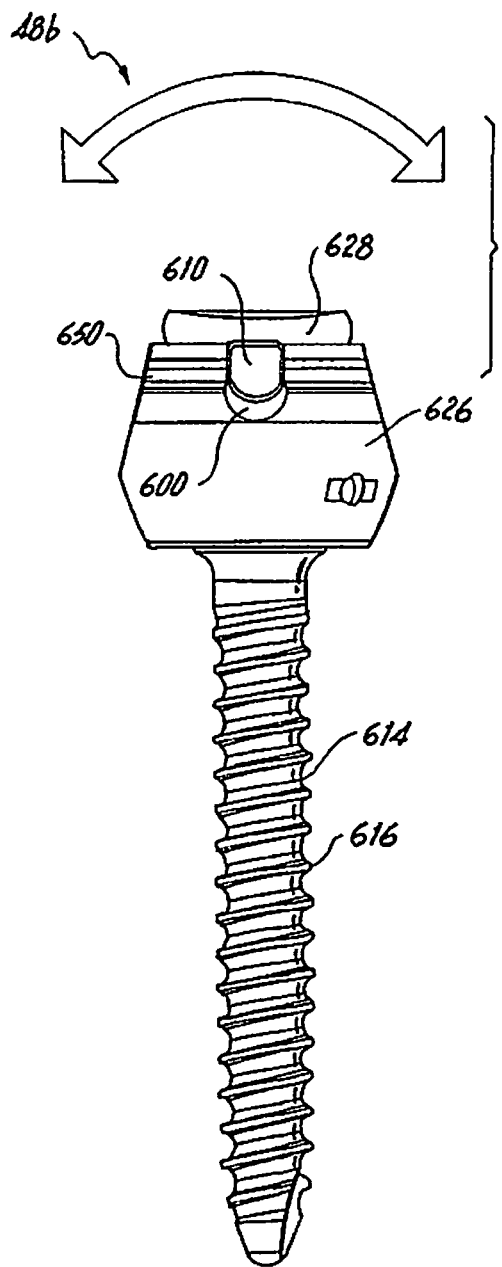
FIG. 5A is a side view of a uniplanar taper lock screw with a coupling in a first position.
Figure 5B:
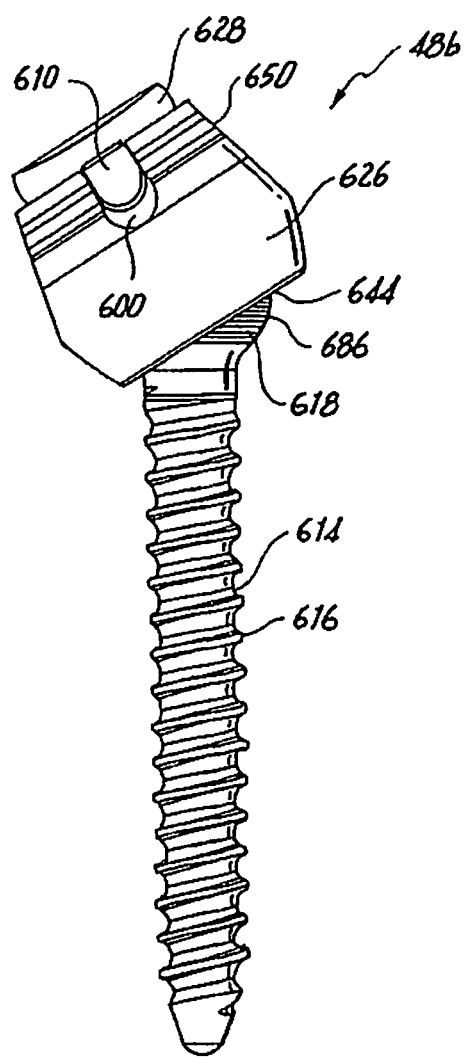
FIG. 5B is a side view of the uniplanar taper lock screw of FIG. 5A with the coupling in a second position.
Figure 6:
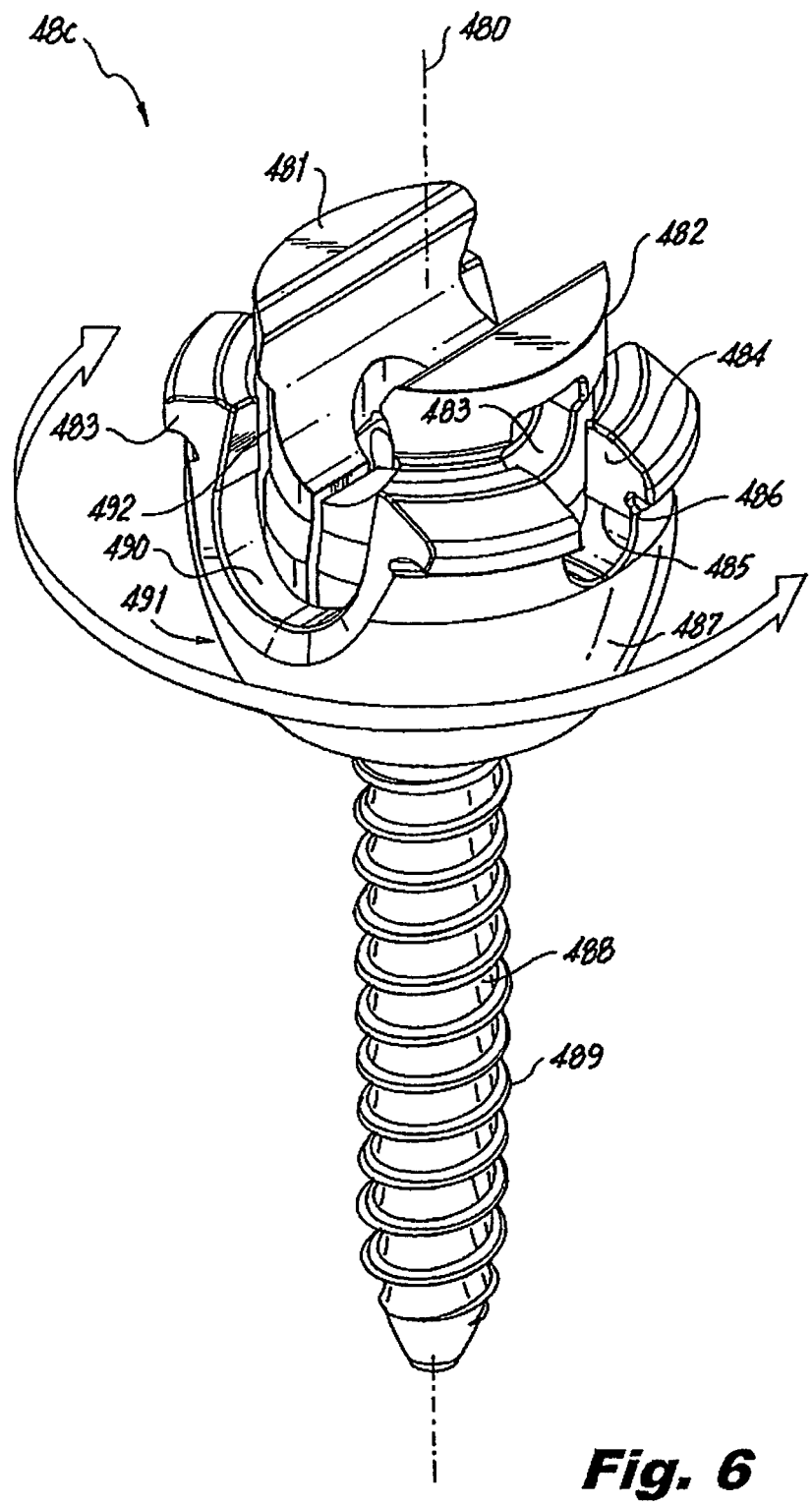
FIG. 6 is a perspective view of a monoaxial taper lock screw.

The rotation of the controlling member 14 drives the attached rod contact member 26 downward. As shown in FIGS. 3 and 17, the rod reduction device 10 is readily connected to the head of a bone screw 48. Further reference to bone screw 48 includes the embodiments of the bone screw 48 that are illustrated in FIGS. 4-6 and discussed in further detail hereinafter. When the screw grasping elements 22, 24 have bone screw 48 positioned therebetween, and the head of the screw 48 (FIGS. 4-6) is engaged with rod 50 (FIG. 3), the downward movement of the rod contact member 26 forces or urges the rod 50 into the head of the bone screw 48. Downward movement of the rod contact member 26 also further secures the head of the bone screw 48 by moving the grasping members 18, 20 inwardly towards each other. Rod reduction is achieved when the rod contact member or anvil 26 is retracted proximally and the rod 50 is placed through the grasping members or arms 18, 20 of the rod reduction device 10. As the anvil or rod contact member 26 is advanced distally, the rod 50 is reduced. Alternatively, a rod locking instrument that mounts over the rod reduction device 10 may be used to partially or fully lock screw 48 while the rod reduction device 10 is mounted to screw 48.

Figure 19:
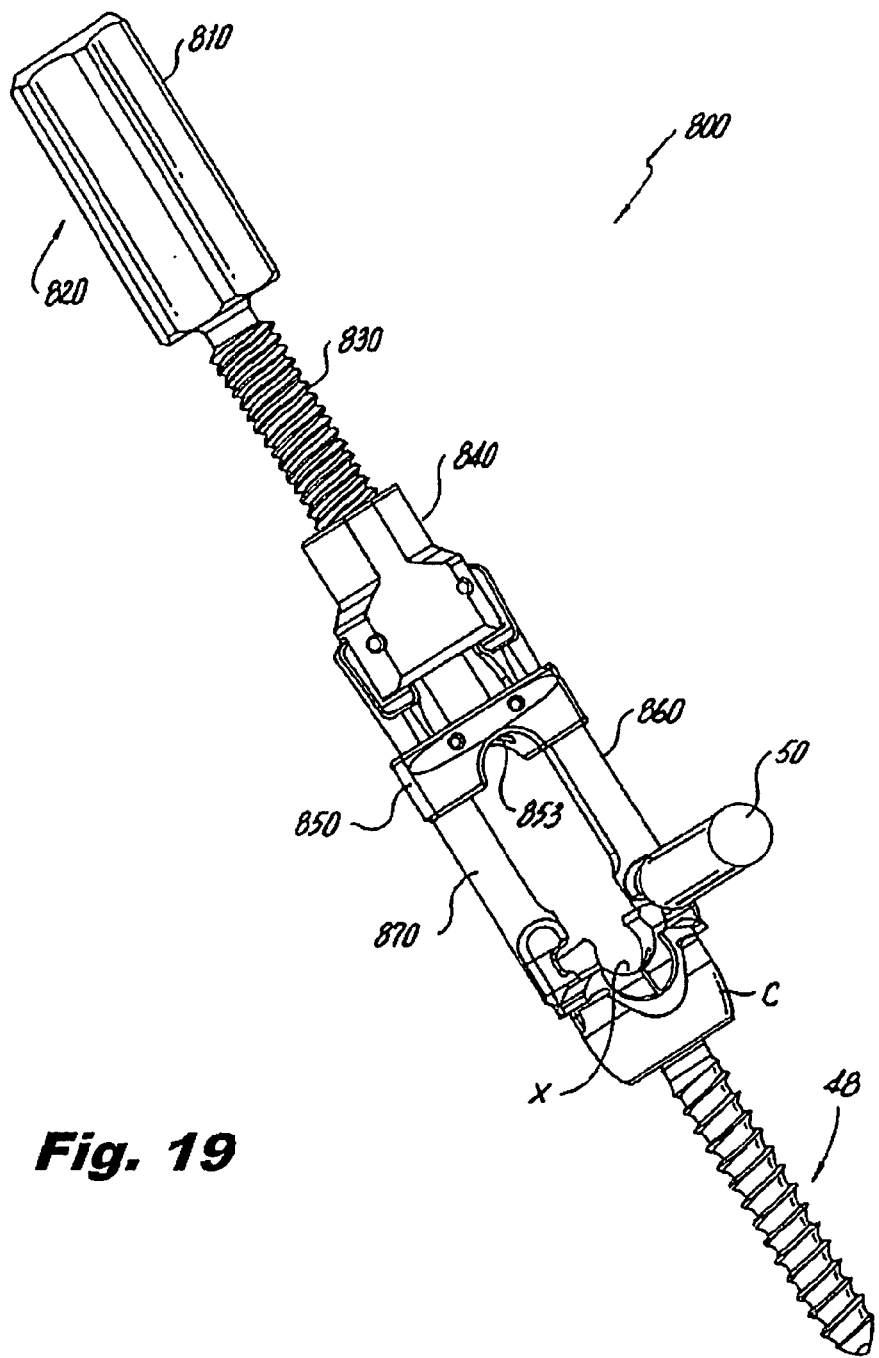
FIG. 19 is a perspective view of a reduction screw engaging an alternative embodiment of a rod reduction device.

In an alternative embodiment, a rod reduction device 800 shown in FIG. 19 may be substituted for the rod reduction device 10. The rod reduction device 800 can as selected be used to partially lock or fully lock the head of the bone screw 48 in position with the rod 50. The spinal rod 50 may be introduced between two arms 860, 870 of the rod reduction device 800 and above saddle X of the bone screw 48. Application of a torsional force to a reduction screw 820 results in a controlled and measurable incremental linear advancement of the reduction screw 820. Reduction screw 820 has a head 810 disposed on the proximal end thereof for driving the reduction screw 820 and a threaded portion 830 through a housing 840 and an anvil bore 853 of the anvil 850. As the reduction screw 820 is advanced, it passes through anvil bore 853 until it contacts the spinal rod 50. Further advancement of the reduction screw 820 reduces the spinal rod 50 into saddle X of the bone screw 48 as well as continues to drive anvil 850 distally. Use of the rod reduction device 800 facilitates axial derotation without locking the bone screws 48. Performing compression and distraction with the bone screws 48 in an unlocked position may be desirable in certain situations, e.g., where the patient has poor bone quality. An example of a suitable rod reduction device is disclosed in International Application No. PCT/US09/47002, filed Jun. 11, 2009, the entire contents of which are hereby incorporated by reference.

The fork assembly body 27 also defines opposing first and second pivot slots 77, 86 configured to pivotally receive first and second opposing elongated grasping members 18, 20 of the fork assembly 21. The fork assembly body 27 defines first and second body through holes 71, 70 configured and adapted to receive first and second body pins 72, 74, which serve as assembly pins for the fork assembly 21 and also serve as pivot pins to permit limited pivotal movement of the first and second elongated grasping members 18, 20 during operation of the rod reduction device 10. This limited pivotal motion is facilitated by pins 72, 74 insertion through appropriately sized grasping member pivot holes 76, 78, which are provided in each of the proximal ends of the elongated grasping members 18, 20.

The rod reduction device 10 can also be employed with an elongated tubular extender (not shown) that fits over the rod reduction device 10. The elongated tubular extender provides additional leverage for selective manual manipulation of the rod reduction device 10 and the bone screw 48 that is embedded in a vertebra V of the spinal column S. At any point when the rod reduction jacks 12 are positioned on the screws 48 with the screws 48 in an unlocked or in a partially locked position, the elongated tubular extenders can be fitted over rod reduction device 10 for improved manual leverage and to facilitate translation.

Figures 2A, 2B:
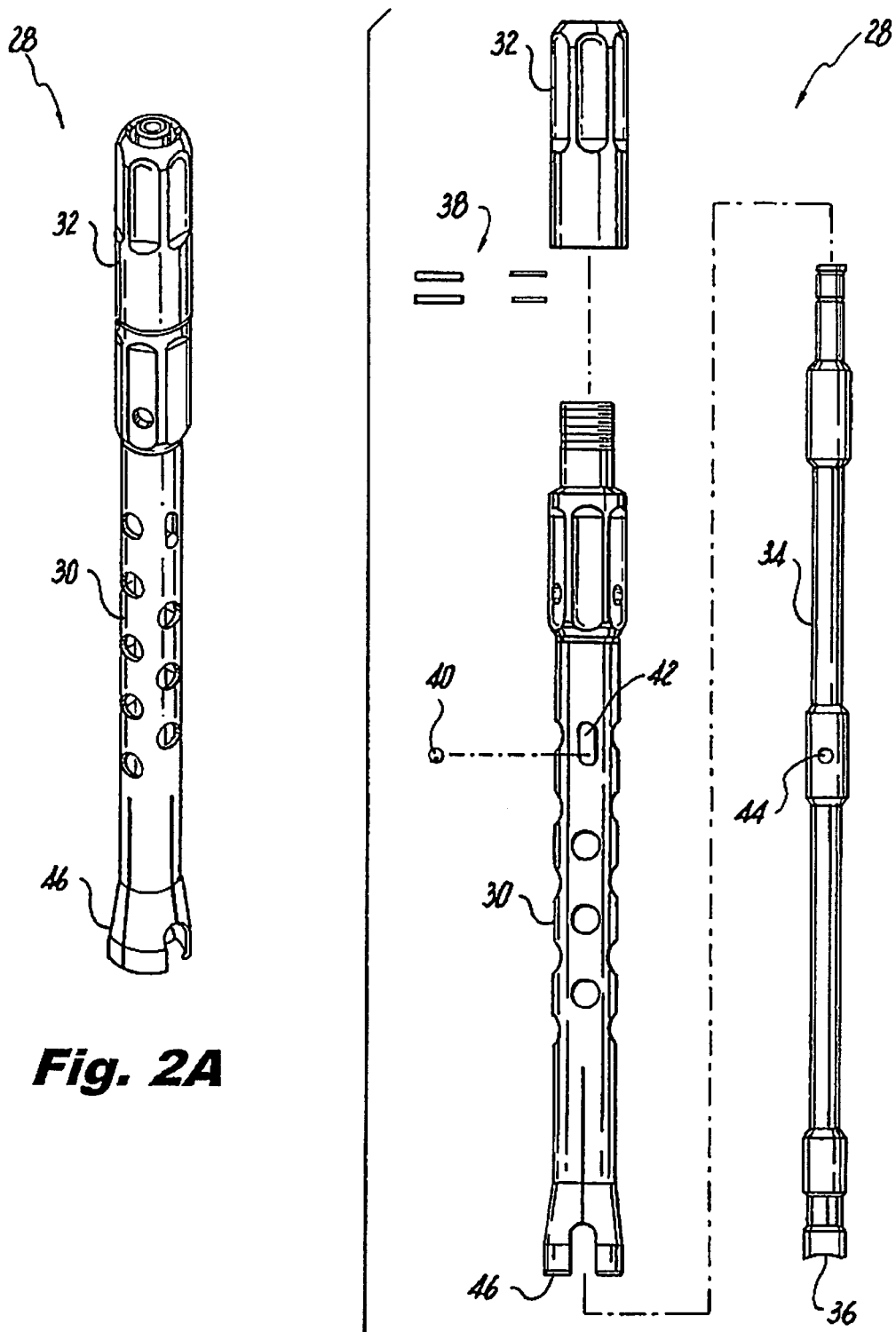
FIG. 2A is a perspective view of a manipulating device.
FIG. 2B is an exploded view, with parts separated, of the manipulating device of FIG. 2A.

A manipulator 28 will now be described with reference to FIGS. 2A and 2B. The manipulator 28 includes an elongated external shaft 30 threadably engaged with a control knob 32. Between the control knob 32 and the elongated external shaft 30, assembly rings 38 may be positioned. An activation rod 34 is slidably contained within the elongated external shaft 30. The activation rod 34 includes a spinal rod contact element 36 at a distal end thereof. A guide pin 40 is adapted and configured to be securely placed within a guide pin receptacle 44 defined within a central section of the activation rod 34. A guide pin slot 42 is defined along a wall of the elongated external shaft 30 and is adapted and configured to define the range of motion of the guide pin 40.

The manipulator 28 is adapted and configured to grasp the head of the bone screw 48. The manipulator 28 is adapted and configured to provide a long moment arm such that the bone screw 48 and the spinal rod 50 can be more easily manipulated and repositioned. A screw grasping member 46 is defined at a distal end of the manipulator 28 and is configured and adapted to engage a bone screw having a taper lock configuration. Downward movement of the activation rod 34 caused by rotating control knob 32 relative to external shaft 30 urges a spinal rod into position in the receiving groove of a bone screw. Continued downward movement of activation rod 34 by that same downward force releases the bone screw grasping member 46 from the head of the bone screw.

Figure 2C:
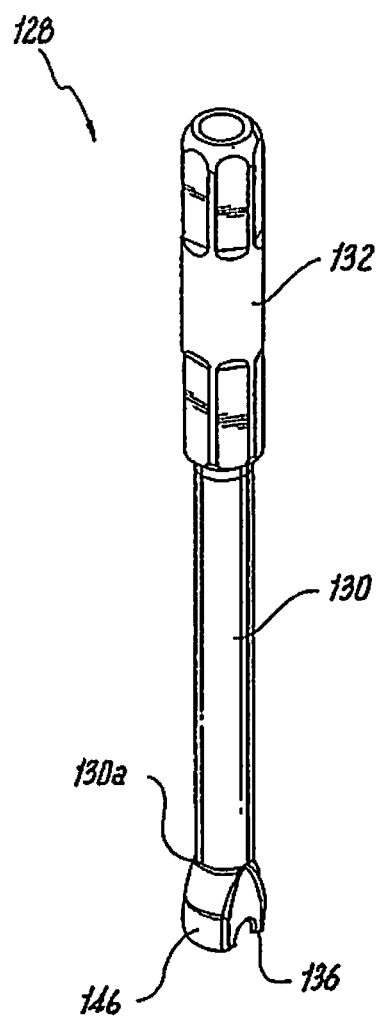
FIG. 2C is a perspective view of another embodiment of a manipulating device.

An alternate embodiment of a manipulator will now be described with reference to FIG. 2C. Manipulator 128 has a distal end 130a having a fixed size. The distal end 130a includes a screw grasping member 146 and a spinal rod contact element 136. Screw grasping member 146 is configured and adapted for engaging a bone screw that uses a setscrew for securing a spinal rod to the bone screw. In addition, the manipulator 128 includes a shaft 130 and a control knob 132 disposed at a proximal end of the screw grasping member 146.

Throughout the disclosure, bone screw 48 refers to any suitable bone screw. It is within the scope of the present disclosure to employ screws having a setscrew or locking nut rod locking or posted configuration, which are limited to uniaxial or monoaxial adjustment. The bone screws 48 may be selected from, inter alia, the group including polyaxial screws 48a (FIGS. 4A-4B), uniplanar screws 48b (FIGS. 5A-5B), and monoaxial taper lock screws 48c (FIG. 6).

Bone screws 48 and spinal rods 50 suitable for the practice of the disclosed surgical method are described herein. Suitable multiplanar taperlock screws are shown and described in U.S. Patent Application Publication 2008/0027432 and in U.S. Patent Application Publication 2007/0093817, both of which are herein incorporated by reference in their entireties.

In particular, the multiplanar taper lock screw is configured to be releasably connected to a spinal rod at an uppermost portion of the screw and physically connected to a first vertebra using a lower threaded portion of the screw. The multiplanar aspect of the screw enables it to be used to make such a connection to the spinal rod that can also be connected to an adjacent vertebra not in the same plane as the first vertebra. The multiplanar taper lock screw includes a proximally located easily accessed flange that is configured to facilitate grasping of the screw by a locking and/or unlocking instrument that can insert and lock a spinal rod securely into place in the screw or selectively unlock the rod from the screw using complementary designed unlocking instruments.

Figure 4B:
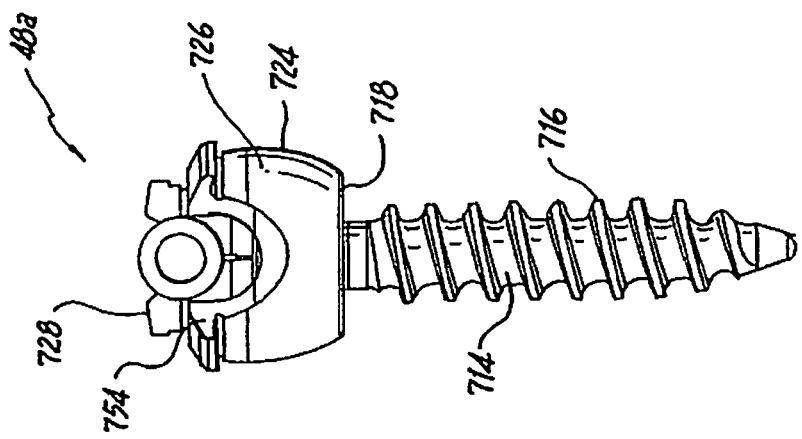
FIG. 4B is a side view of the polyaxial screw and spinal rod of FIG. 4A in a locked state.
Figure 4A:
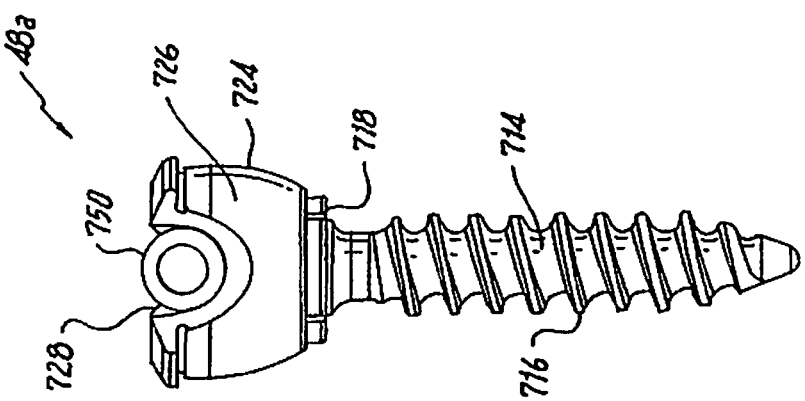
FIG. 4A is a side view of a polyaxial screw with a spinal rod in an unlocked state.

Polyaxial bone screws, such as screws which lock to a rod by means of a setscrew or locking nut as are known in the art, can also be selectively used as described below. While the referenced uniplanar and monoaxial taper lock bone screws are suitable for use in the current method, it is envisioned that any bone screw that functions to limit movement to a single plane or to a single axis of rotation and also possess the capability to be partially locked and/or fully locked with similar ease as the referenced screws would be suitable for use. Polyaxial bone screw 48a is shown in FIGS. 4A and 4B. The polyaxial bone screw 48a includes a screw shaft 714 defining a helical external thread 716 thereabout and a screw head 718 attached to an upper portion of screw shaft 714. A dual layered screw housing 724 is positioned partially around screw head 718. Screw housing 724 has an outer housing 726 and an inner housing 728 configured to move relative to each other. Inner housing 728 defines an aperture 750 dimensioned to receive at least a portion of a rigid elongate member and has at least one compression contact surface 754 configured to compress the rigid elongate member when screw 48a is placed in its locked position, as shown in FIG. 4A. The rigid elongate member, e.g., rod 50, may be removed from aperture 750 by sliding inner housing 728 away from screw shaft 714, such that the screw 48a is in an unlocked position, as seen in FIG. 4B.

Suitable uniplanar taperlock bone screws are shown and described in U.S. Patent Application Publication 2009/0105769, the entire contents of which is hereby incorporated by reference. A uniplanar taperlock bone screw 48b is shown in FIGS. 5A and 5B. The uniplanar bone screw 48b in a partially locked or unlocked configuration allows uniplanar pivotal movement of an outer housing 626 and inner housing 628 relative to a bone screw shaft 614, which defines an external helical thread 616 for penetrating cancellous bone through the application of torque. This limited pivotal rotation facilitates positioning of a connecting rod to the screw 48b and allows for manipulation of the spinal column as needed. Importantly, the flexibility of the connecting rod position relative to the inserted bone screw in one plane while restricting movement in all other planes allows only selected movement of the screw head-connecting rod attachment prior to locking the system in place. The surgeon's manipulation forces on the spinal column are more effective in properly positioning the spinal column because, while the uniplanar pivotal movement of the screw head-connecting rod attachment facilitates rod positioning and attachment, the complete restriction of movement of that attachment in any other plane serves to direct the applied manual force to its intended purpose, that of manipulating and realigning the spine. Failure to limit all other movement of the connecting rod-screw head attachment during the manipulation of the spine could instead result in the head of the screw pivoting or rotating over to one side or the other relative to the longitudinal axis of the spinal screw. The uniplanar screw head effectively restricts movement to a single plane and thus avoids the undesirable multiplanar movement of the screw head during manipulation of the spine.

The uniplanar taperlock bone screw 48b can be provided with an inner housing access slot 600 defined through a wall of outer housing 626, which provides access for an unlocking tool designed to make grasping contact with an inner housing tool receptor 610 to facilitate quickly unlocking the screw 48b and permit movement of head 618 within an articulation recess and removal of a rod from the inner housing connecting rod slot. The screw head 618 may have a textured surface 686, which can serve to provide a degree of limited resistance to the operation of the uniplanar articulation provided by the screw 48b. A screw articulation recess is defined in an interior of a lower portion of the inner housing 628 that has an interior surface having a complementary surface configuration to the generally spherical shape of the screw head 618 so as to facilitate articulation of the screw head 618 within the recess. The lower most portion of the inner housing 628 defines a screw shaft exit portal 644 that is configured and adapted to retain the spherical screw head 618 within the recess while allowing uniplanar rotational movement of the screw shaft that extends exterior to the inner housing 628. The screw 48b can be provided with an inner housing access slot 600 defined through a wall of the outer housing 626, which provides access for an unlocking tool designed to make grasping contact with an inner housing tool receptor 610 to facilitate quickly unlocking the screw 48b and permit movement of the screw head 618 within the articulation recess and removal of the connecting rod from rod slot 650.

Suitable monoaxial taperlock bone screws are shown and described in U.S. Patent Application Publication 2009/0105716, the entire contents of which is hereby incorporated by reference. In particular, the monoaxial taper lock screws have flexibility along a single axis to facilitate attachment of connecting rods to the screws for treatment of certain spinal conditions, such as scoliosis, that require manual realignment or positioning of the spinal column prior to locking the spinal column into a selected position. A monoaxial screw 48c, as shown in FIG. 6, in a partially locked or unlocked configuration allows monoaxial rotational movement of an outer housing 487 and inner housing 481 around a longitudinal axis 480 and a bone screw shaft 488, which defines an external helical thread 489 for penetrating cancellous bone through the application of torque. This articulation of the screw head facilitates positioning of rod 50 to the screw 48c and allows a surgeon to manipulate the spinal column as needed. Importantly, the flexibility of the position of the rod 50 relative to the inserted screw 48 in one plane while restricting movement in all other planes allows only selected movement of the screw head and rod attachment prior to locking the system in place. Manipulation forces on the spinal column are more effective in properly positioning the spinal column because, while the monoaxial pivotal movement of the screw head and rod attachment facilitates rod positioning and attachment, the complete restriction of movement of that attachment in any other plane serves to direct the applied manual force to its intended purpose, that of manipulating and realigning the spine. Failure to limit all other movement of the rod and screw attachment during manipulation of the spine could instead result in the head of the screw 48 pivoting or rotating over to one side or the other relative to the longitudinal axis of the screw 48. The head of the monoaxial screw 48c effectively restricts movement to a single plane, perpendicular to the longitudinal axis 480 of the screw 48c, and thus inhibits undesirable multiaxial movement of the screw head during spinal manipulation.

The monoaxial screw 48c, as shown in FIG. 6, is capable of connecting to the spinal rod 50 by the use of a dual layered screw housing 491 that includes an outer housing 487 and an inner housing 481. The outer housing 487 is configured such that at least a portion of the inner surface 492 of the outer housing 487 is capable of selectively sliding over a potion of an outer surface 482 of the inner housing 481 in an upward and downward direction along the longitudinal axis of the screw 48c. An inner housing access slot 483 is configured and adapted to facilitate quick unlocking of screw 48c and movement of the head of the screw 48c within an articulation recess and removal of the rod 50 from an inner housing rod slot. The outer housing 487 can include an annular gripping groove 486. An outer housing connecting rod slot 490 is also provided that is in common alignment with an inner housing connecting rod slot but is not necessarily of exactly the same measurement as the inner housing slot.

Additional surgical instruments and tools can be provided to facilitate the practice of the methods discussed herein. Such instruments include, for example, a rod reduction device such as, for example, that disclosed in U.S. Patent Application Publication 2007/0093849 that facilitates single action anti-torque rod reduction, the entire contents of which is herein incorporated by reference. Any device capable of easily grasping the head of a taper lock bone screw, and reduce a spinal rod into position in the receiving groove of the bone screw could also be used in the current spinal surgery method. Other tools and devices such as screwdriver type devices and spinal rod end grasping manipulating levers, or other surgical tools and devices known in the art can also be used to facilitate the current spinal surgery method. By way of further example, a dual action rod reducer and locker as shown and described in U.S Patent Application Publication 2007/0213722, the entire contents of which is hereby incorporated by reference herein is also suitable for use in the methods currently disclosed. In particular, a dual action surgical device capable of reducing a rod into position in a rod receiving notch in the head of a bone screw with a first action and subsequently locking the rod into the receiving notch by a second action of the same instrument may be used.

Suitable screw locking and unlocking devices are also shown and described in U.S. Patent Application Publication 2007/0093817. In particular, a multi-planar taper lock screw for connecting a connecting rod to bone and a locking and unlocking device configured to selectively partially lock or fully lock the screw may be used. The multiplanar taper lock screw may be capable of multi-directional articulation while the connecting rod position can remain stable and aligned as needed. After the screw had been articulated and properly positioned, it can be locked such that the screw and the connecting rod will remain in relative position to the bone.

The methods described herein can be utilized to correct any spinal deformity involving a convexity and a concavity. Depending upon the nature of the deformity, a suitable bone screw 48 will be selected for use, e.g., polyaxial bone screws 48a, uniplanar bone screws 48b, and/or monoaxial bone screws 48c. The bone screws 48 are first implanted into the vertebra of the spinal column S at multiple points above and below the apex A of the curve. Rod reduction devices 10 including a screwjack mechanism 12 and manipulation devices 28 adapted and configured for attachment to heads of the taper lock bone screws 48, and which provide leverage to facilitate the manipulation of the spine S, can then be attached to the heads of the bone screws. As seen in FIG. 3, the rod reduction device 10 is attached to the heads of the bone screws 48 on the concave side S1 of the spinal deformity. The manipulator device 28 is placed on the bone screws 48 on the convex side S2 of the spinal deformity. Depending upon the nature of the deformity, the rod reduction device 10 can be used on both sides of the deformity.

Prior to any correction of the rods 50, the surgeon can manipulate and correct the curve of the spinal column S to a large degree. That is, the surgeon can first manually manipulate and reduce the "rib hump." The spinal rod 50 can be pre-bent to the configuration of the normal spinal curve, e.g., the sagittal curve. Once certain the spine S is in the proper anatomical position, the surgeon can position the pre-bent spinal rods 50 relative to the screws and the rod reduction devices, and lock each rod 50 to the first two points of the spinal column where the construct is to be attached.

By way of example, in a Single Thoracic (Right T4-L1) spinal deformity, the spinal rods 50 can first be attached to vertebrae T4 and T5. This proximal attachment is accomplished using polyaxial bone screws for ease of rod attachment and to establish a proximal foundation for the construct. These initial proximal attachments at T4 and T5 can be partially locked into position to provide stability for further work during surgery to build the construct and manipulate the spine for correction. Other screw attachments to the other vertebrae can be accomplished using uniplanar taper lock screws 48b (FIGS. 5A-5B) although the lowest instrumented vertebra (LIV) should be provided with a mono-axial taper lock screw 48c (FIG. 6). Once attached to the vertebrae, the remaining unlocked bone screws are ready to be connected to rod reduction devices 10 on the concave side S1 of the deformity and the manipulator devices 28 on the convex side S2 of the deformity, as seen in FIG. 3. The pre-bent spinal rod 50 configured to have a physiological sagittal plane can then be threaded through the unlocked bone screws and the attached reduction devices 10.

In an embodiment, the reduction devices 10 are sequentially tightened, alternating from the ends toward the middle or from one end to the other, depending upon the surgeon's technique to reduce the spinal rod 50 into the head of the bone screws 48. It is noted that the reduction devices 10 may also be contemporaneously tightened and need not be tightened sequentially. As the reduction devices 10 tighten, the action of the screw jack mechanism 12 will gradually reduce the spinal rod 50 while effecting any rotation of the spinal column S needed to bring the spinal column into proper alignment. The effect of rod reduction and rotational correction in a single action serves to facilitate the improved efficiency and effectiveness of the spinal correction method. As discussed in greater detail below, at or near completion of the reduction of the spinal rod 50, the taper lock bone screws 48, either uniplanar or mono-axial, can be partially locked into position by the mechanism of a locking device such as rod reducer 10.

A partial locker 60 can be used to engage the bone screw 48 and lock the rod 50 into place. The partial locker 60, shown in FIGS. 7A and 7B, includes screw grasping elements 61, which are configured to grasp the bone screw 48. In operation, an inner locking shaft 62 is slidably disposed within a housing 64 and can be moved by a pivotally mounted activation handle 66 such that a contact end 68 of the shaft 62 is brought into operational contact with the proximal end of the rod reduction device 10 while the grasping elements 61 pull the outer housing of the screw 48 upward over the screw inner housing into a partial or fully locked position.

The partial locker 60 mounts over a rod reduction jack 12 to enable partial locking of the taper lock screw to the rod 50 prior to removal of the rod reducer 10 from the screw 48, as shown in FIG. 7C. The rod reducer 10 is then removed from the screw 48. At this point, the partially locked polyaxial bone screws 48a (FIGS. 4A-4B) attaching the rods 50 to T4 and T5 can be fully locked with any suitable locking instrument. In all the disclosed embodiments, attaching a spinal rod 50 to a pedicle screw may be accomplished as discussed hereinabove or it may be accomplished by moving one or more vertebral bodies towards the spinal rod, i.e., translation of the screw 48 towards the spinal rod 50, or by a combination of these techniques.

The spinal rod 50 is seated in the bone screws 48 by gradually tightening the screwjack mechanism 12 of the rod reduction device 10. This action may be performed sequentially (or contemporaneously) on the vertebrae from either end of the construct toward the apex A of the deformity and simultaneously gradually translating and derotating the spinal column S into the desired physiological sagittal curve. It is noted that by performing the translation gradually and sequentially with several rod reduction devices 10, numerous screws in the construct are loaded and corrective forces are distributed over numerous screws during the correction, reducing the possibility of a screw pull-out and the resulting loss of fixation which can result from exerting too great a force on one screw at a time during correction. Once all of the rod reduction devices 10 are maximally tightened, the spinal rod 50 will be captured in each of the heads of the bone screws 48. Also, during this sequence of maneuvers counter-torsion of lowest instrumented vertebra (LIV) is accomplished.

At any point during correction, the surgeon may utilize the rod reduction device 10 and the partial locker 60, discussed above, or a similar taper lock bone screw locking device to one or more screws to partially lock a screw. By or at the end of the reduction of the rods 50 into all the bone screws 48, the partial locker 60 will have been or will be applied to all bone screws 48 to which rod reduction devices 10 are attached so that the spinal rod 50 is partially locked to all the bone screws 48.

With screws 48 in a partially locked position, the corresponding rod reduction devices 10 can then be removed from the bone screw 48 on the concave side S1 of the deformity. The rod reduction devices 10 having been removed from the screws 48 on the concave side S1 of the deformity are then placed on the heads of the screws 48 on the convex side S2 of the deformity. The pre-bent spinal rod 50 can then be introduced into the convex side S2 in a similar fashion to the earlier introduction of the spinal rod 50 into the concave side S1 of the deformation. Sequential tightening of the rod reduction devices 10 on the convex side S2 of the deformity can be gradually accomplished as before until the translation and rotation has been achieved for the convex S2 side. At this point, in situ adjustments may be made to the spinal rod contour.

With the screws implanted and partially locked to the rods 50, final deformity correction including compression, distraction, and/or direct vertebral derotation can be accomplished. Any such final corrections can be performed from either end of the construct toward the apex A of the deformity. Application of a suitable screw locking system, such as the rod reduction device 10 and partial locker 60, to the heads of screws 48 can be performed to maintain the earlier achieved corrected rotation on the concave side S1. The application of compression between the convex side S2 of the bone screws 48 and a proximal fixation point (or against a rod manipulator 700 shown in FIGS. 18 and 18A) can be performed to level the motion segment. Following this, a locking instrument, such as partial locker 60, can be used to lock the convex side fixation points or screws 48 to the rod 50 on the convex S2 side. At this point, the derotation/compression procedures described above may be applied beyond the apex A of the deformity until the desired correction is achieved. Again, the rod manipulator 700 can be applied to buttress the locked bone screws 48.

Figures 18, 18A:
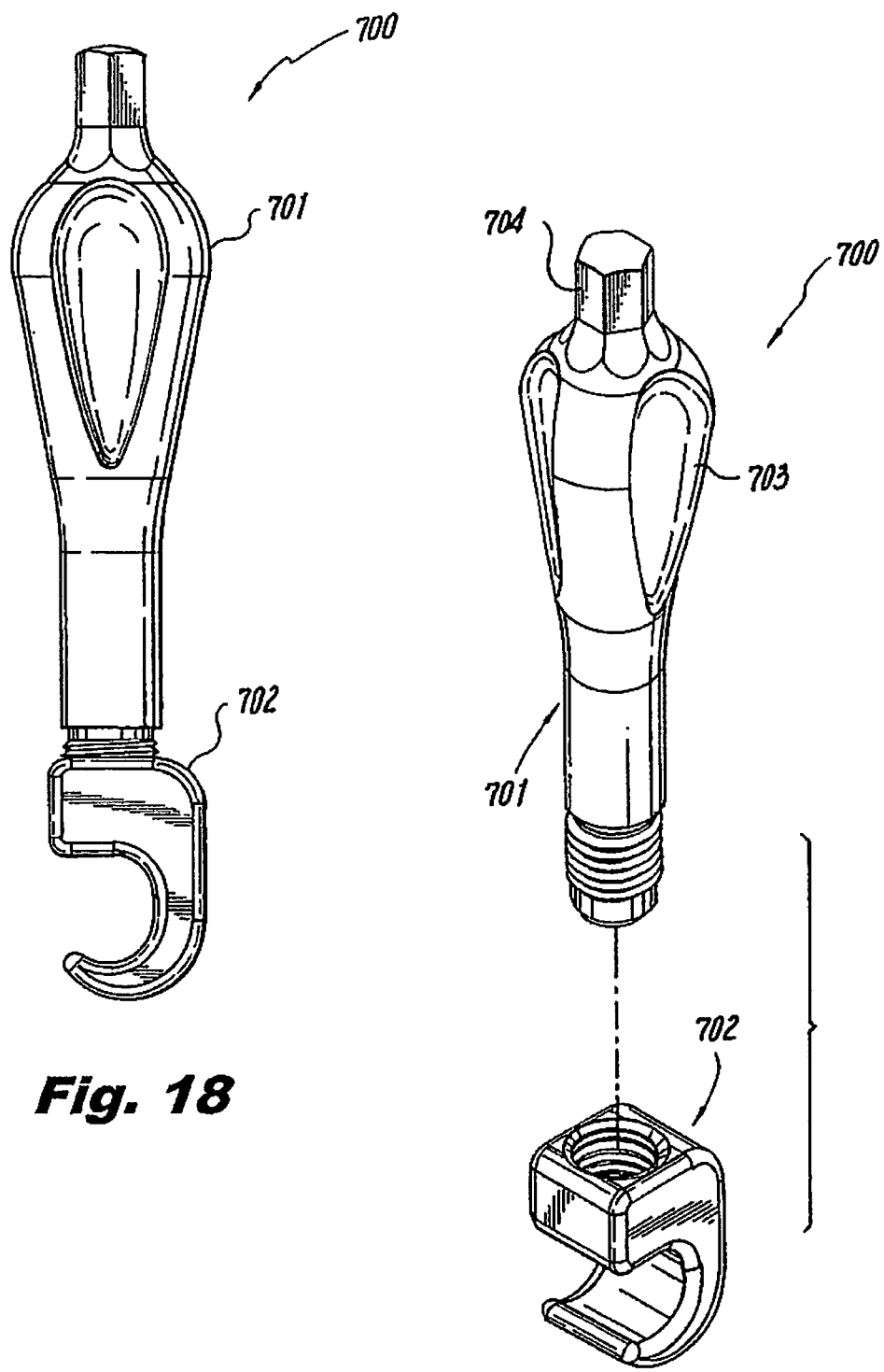
FIG. 18 is a front view of a rod manipulator.
FIG. 18A is an exploded isometric view of the rod manipulator of FIG. 18.

The rod manipulator 700, illustrated in FIGS. 18 and 18A, may be used to facilitate distraction or compression in the absence of a fully locked bone screw 48 in the location where that procedure is to be performed. The rod manipulator 700 includes a grasping element 702 configured and adapted to engage spinal rod 50. The grasping element 702 may be threadably coupled to an elongated structure 701 adapted and configured to provide leverage. The elongated structure 701 may be configured to be manipulated and grasped by a surgeon. Gripping element 703 may facilitate manual manipulation of the rod manipulator 700. In addition, the proximal end 704 of the rod manipulator 700 may be configured and adapted to engage a screwdriver type device (not shown) having a corresponding shape.

Finally, the horizontal position of the lowest instrumented vertebra (LIV) can be confirmed and at those fixation points, the screws 48 can be fully locked if previously only partially locked. A locking instrument, e.g., partial locker 60, can be reapplied to each fixation point or screw head to confirm rigid fixation throughout the construct. Any remaining rod manipulators 700 can be removed at this time and the spinal method is completed. Bone graft material can be added as needed and any cross-links for rods 50 can be applied if appropriate. Normal irrigation, decortication of the fusion bed, and other normal closing procedures can be performed at this time. Alternative embodiments of the method, depending inter alia upon the presentation of the deformity, are within the scope of the present disclosure.

The number of uniplanar screws required is dependent upon the magnitude of the curvature of the spinal deformity. Furthermore, the number of Ponte osteotomies depends upon the degree of flexibility of the curve. Selection of an appropriate material for the formation of the spinal rod R can be based upon a determination of bone stock and fragility.

An alternative method of practicing the disclosed spinal surgery procedure for a Single Thoracic (Right T4-L1) is similar to the above described method with a few revisions that will now be discussed. Unlike the earlier discussed method, the selection of bone screws 48 does not include a monoaxial bone screw for the last instrumented vertebra (LIV). Polyaxial bone screws including but not limited to taper lock, set screw, locking nut or similar screws, are similarly used to establish a proximal foundation at T4 and T5, however uniplanar bone screws are used for all other fixation points in the construct. Rod reduction devices 10 are applied bilaterally at T4 and T5. Spinal rods 50 are introduced into the rod reduction devices 10 bilaterally.

After ensuring sagittal alignment of the spinal rods 50, the screws 48 at T4 and T5 are fully locked using a suitable locking instrument among those previously identified. Rod reduction devices 10 are then applied over both spinal rods 50 to capture the apical screws and reduce the rod 50 on the convex side S2 into the bone screws 48. The rod 50 may be sequentially reduced. At this point, the bone screws 48 on the concave side S1 are partially locked using the partial locker 60, shown in FIGS. 7A and 7B, and the rod reduction devices 10 are removed. At this point, the method proceeds to the earlier discussed final deformation correction steps. The bilateral application of many of the steps alters the method somewhat from the earlier described method wherein first the concavity of the deformity was dealt with followed by the applications to the convex side S2 of the deformity.

In a thoracolumbar/lumbar spinal deformation presentation, the method initially described is varied to some degree in that the rod reduction devices 10 are applied to the bone screws 48 bilaterally rather than first to the concave side S1 and second to the convex side S2 of the deformity. Extenders to the rod reduction devices 10 are also applied bilaterally. The spinal rod 50 is introduced initially only to the convex side S2 of the deformation. The LIV is stabilized by partially locking the screw to the rod 50 and the vertebrae above the LIV are manually rotated using the improved leverage offered by the attachment of the extenders to the rod reduction devices 10. Derotation of the spinal rod 50 on the convex side of the deformity is then accomplished. The LIV is further secured by being fully locked. At this point, the spinal rod 50 is introduced to the concave side of the deformity and it is derotated. The screws 48 are subsequently locked to the rod 50 using a suitable locking device. The rod reducing devices 48 are then removed from the concave side S1 of the construct. Distraction is accomplished both distally and proximally beginning from the apex A of the deformity. The concave side of the construct is then fully locked. At this point, seating of the spinal rod 50 into the heads of the screws 48 on the convex side is accomplished and a partial lock over the rod reducing devices 10 is performed. Compression of the lower apex on the convex side S2 is next accomplished followed by fully locking the convex side S2 of the construct.

In a double thoracic (curves Left T1-T4, Right T4-L-1) presentation of the spinal deformity, the disclosed spinal surgery method is also accomplished with some revisions and adjustment of the steps discussed earlier with respect to the single thoracic method. In the double thoracic deformity, polyaxial screws are employed at T1, T2, or T3 to establish a proximal foundation. Similarly to the single thoracic method, uniplanar screws are used for all fixation points in the construct with the exception of a monoaxial screw being used at LIV. Procedures of seating the rod 50 and subsequently rotating the rod 50 are followed by achieving a partial lock in the proximal fixation points (T2-T5) by using the partial locker 60 shown in FIGS. 7A and 7B and rod reduction devices 10 or by using the second handle of a dual action rod reducing and locking device, as shown and described in U.S. Patent Application Publication 2007/0213722. The T-2 fixation point can be fully locked at this time using a locking instrument, such as the torqueless locking instrument that can insert and lock a spinal rod securely into place in the screw or selectively lock/unlock the rod from the screw and is configured with complementary features to that of the multi-planar taper lock screw, as shown and described in U.S. Patent Application Publication 2007/0093817. Segmental compression between the now fully locked T-2 and partially locked T-3 fixation points, repeated between the upper curve segments (T-2-T-5 or T-6) effect a correction in the upper thoracic curve.

At this point, rod reduction devices 10 can be applied over the concave rod 50 to capture the bone screws 48 on the concave side S1 of the deformity from T-6 to L-1. As with the originally described general method, the spinal rod 50 can be seated into the distal bone screws 48 by gradually tightening the rod reduction devices 10 and the sequential derotation and translation of the spine to the spinal rod 50 on the concave side S1.

Figure 7A:
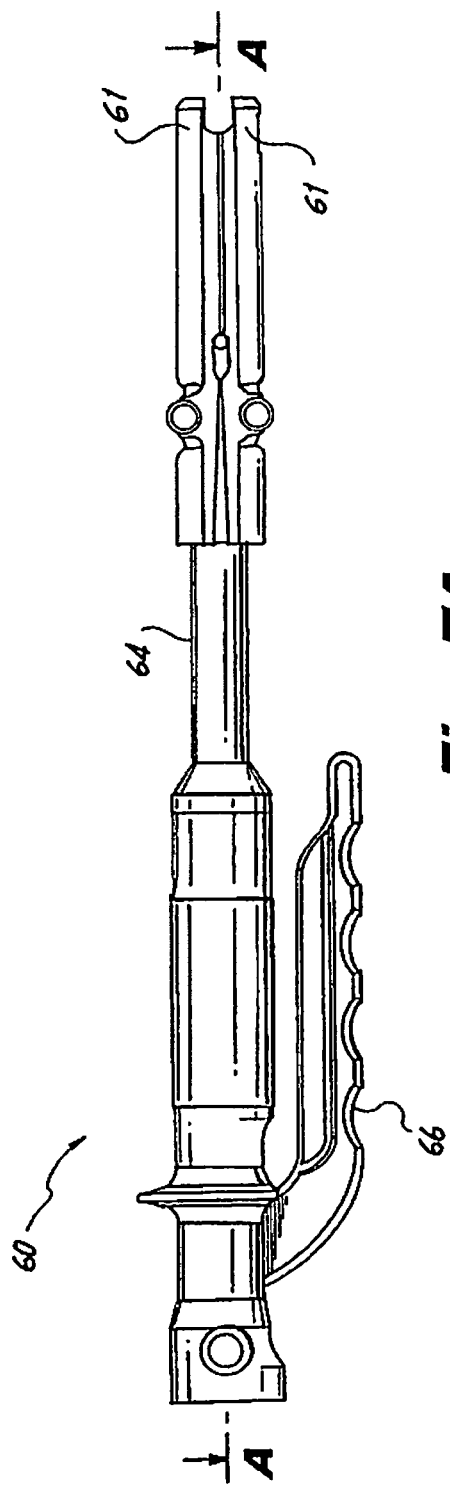
FIG. 7A is a side view of a screw locking device.
Figure 7B:
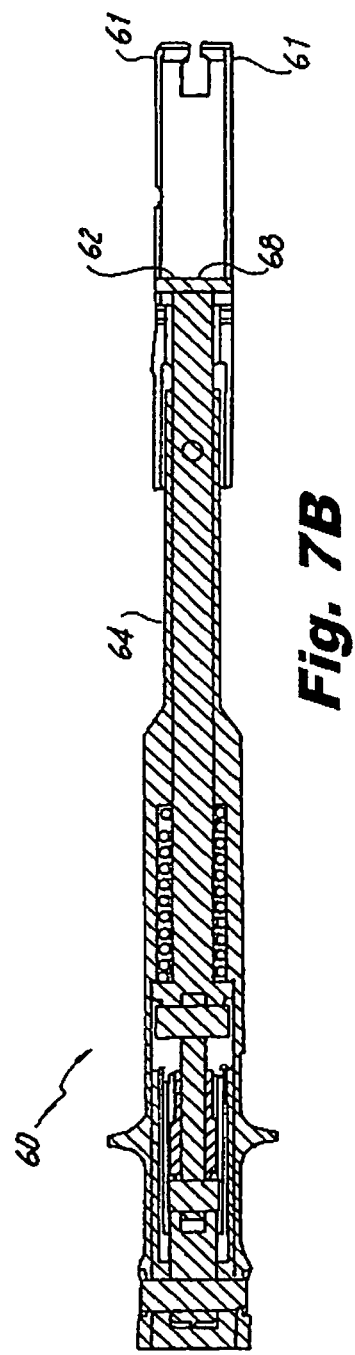
FIG. 7B is a cross-sectional view of the screw locking device of FIG. 7A taken along section line A-A.

All the fixation points or bone screws 48 on the concave side S1 can be partially locked over the rod reduction devices 10 using the locker shown in FIGS. 7A and 7B. As with the originally described embodiment of the method, the rod reduction devices 10 can now be removed from the bone screws 48 of the concave side S1 and affixed to the bone screws 48 of the convex side S2 of the deformity. The above sequence of steps is similarly repeated for the convex side S2 of the deformity and after translating and rotating the convex S2 side, the final deformation correction, as earlier described, can be accomplished. The spinal rod 50 should be placed on the concave side S1 of the lower curve to inhibit fracture of the smaller high thoracic pedicles during reduction.

In a double major (T-4-L4; right thoracic, left lumbar) presentation of a spinal deformity, the steps of the general method are modified to meet the additional problems posed by this presentation. As seen in other variants of the surgical method, polyaxial screws at T4-T5 are used to establish a proximal foundation for the construct. Rod reduction devices 10 are first applied proximally at T4-T6 to the concave side S1 of the thoracic deformity and the spinal rod 50 is introduced to that side. Rod reduction devices 10 can then be applied over the spinal rod 50 at the apex A of both curves of the spinal deformity. The rod 50 on the concave side S1 is then rotated into the sagittal plane and partial locks are applied to T4 and T5. Once the rod reduction devices 10 can be removed at T4 and T5, T5 and T5 can be fully locked using a locking instrument, e.g., partial locker 60.

Rod reduction devices 10 are loosely advanced in the lumbar curve of the deformity and extenders are applied to the convex side S2 of the lumbar curve. At this time, the LIV is stabilized and the mid-apical lumbar is rotated. The spinal rod 50 can then be sealed into the distal fixation screws 48 and a temporary short concave lumbar rod can be partially locked. The rod 50 can be seated into the distal fixation screws 48. Derotation and translation of the spine S to the rod 50 on the concave side S1 can be achieved. Gradual, sequential partial tightening of the rod reduction devices 10 towards the apex A of the deformity can then be accomplished while taking care to avoid screw pull-out. The concave side S1 of the construct can then be partially locked and the rod reduction devices 10 removed from the concave side S1 and placed on the convex side S2. On the convex side S2, the procedures earlier performed for the concave side S1 are repeated with the final deformity correction being accomplished as before described beginning from the proximal end of the construct to the apex A of the deformity. As the method progresses on the convex side S2 of the deformity, the opportunity for in situ correction of the rod 50 can be presented.

With respect to the method provided for a double major presentation, large or particularly stiff curves in the spinal deformity may not be able to be reduced with a single reduction rod. In that case, two smaller rod segments may be used to reduce each curve on the same side of the spine S. In that instance, the rods 50 are then connected together with a side-side "wedding band" connector. A stiff holding rod may then be coupled to the other side. Replacement of the conjoined initial rods is possible. In this presentation, derotation of both the apices on the concave side S1 and convex side S2 of the spinal deformity should be performed simultaneously and in opposite directions to the coupled nature of the rotational deformities.

In a triple curve (thorasic/thracolumbar/lumbar) presentation of a spinal deformity, all three apices should preferably be derotated simultaneously. The method employed in this situation is similar to that of the method described with respect to a double thoracic presentation up to the application of the extenders to the rod reduction devices 10 with the following exceptions that will now be described. Additionally, the steps recited above with respect the thoracic and the distraction steps in the upper thoracic concavity method can be employed. The thoracic convex steps are then required following by the entire lumbar section steps if residual curve or rotation exists.

In a Kyphosis (T2-T3) (Combined techniques) presentation of a spinal deformity, the initial consideration should be to the lordotic lumbar level caudally, and T3-T4 cephalad. Anterior release and interbody distraction is seldom necessary with the newer posterior shortening techniques (Ponte, Pedicle Subtraction osteotomies). The implant selection in this presentation should favor stiffer, stouter materials. As is common with other variants of the spinal surgery method described herein, initial preparation of the surgical field and at least partial exposure of the spinal column requires release of the transverse process ligaments, comprehensive wide facetectomy at all levels with excision of flavum, and multiple Ponte osteotomies symmetrically placed about the apex of the kyphosis is required.

As before, proximally at T-2-T3, polyaxial screws are used for ease of rod attachment and establishment of a proximal foundation. As in the general method, described above, uniplanar screws are used for the remaining fixation points with the exception of the lowest instrumented vertebra (LIV), which requires a monoaxial screw. This variation of the method can alternatively use polyaxial screws for a flexible deformity.

Spinal rods 50 in this deformity can be introduced at T2-T4 using rod reduction devices 10 to seat the rods 50 and the partial locker 60 to achieve a partial lock for the screws 48 with the rod reduction devices 10 in place. At this point, the rod reduction devices 10 can be removed and the head of the screw 48 at T2 can be fully locked using a locking instrument. At this point, the surgeon can compress the fully locked screws 48 at T2 and partially locked screws 48 at T3 bilaterally followed by fully locking screws 48 at T3. Similar segmental compression can be achieved between T3 and T4 to complete the proximal foundation of the reconstruction.

Bilateral application of rod reduction devices 10 to the screws 48 below T4 (from proximal to distal) can be done to capture the spinal rods 50. At this point, the earlier described sequential tightening of the rod reduction devices 10 from proximal to distal ends of the construct to translate the rod 50 down to the spine S while providing corrective rotation can be accomplished gradually with slow progression of the rods 50 into full seating in the heads of the screws 48. Screw pull-out can be inhibited by performing translation simultaneously with several rod reduction devices 10. After partial locking is completed, the rod reduction device 10 can be removed and placed on a more distal screw 48 to facilitate rod translation at sequential fixing points. Sequential compression is completed from the level of T4 down to the lowest instrumented vertebra (LIV) to complete the kyphosis correction. After the horizontal position of the LIV is confirmed, the fixation points can be fully locked using a quick lock instrument. Again, the full locking of each fixation point is confirmed to provide rigid fixation throughout the construct. As a notation, for a severe or rigid deformity, the use of transverse connector(s) proximally prior to apical and distal cantilever and the performance of SPO or apical osteotomies can be carried out to facilitate curve corrections.

Alternatively, for Kyphosis (T2-L3) method described above, a variant method referred to as "focal apical reduction" can be employed. For stiff or severe kyphotic deformities that require greater corrections, the spine S can be pre-corrected with temporary rods (not shown) prior to the placement of the rods 50 that will serve as the final implants at the apex A of the deformity. Such temporary rods can be provided by cutting a soft rod into two segments that are long enough to extend at least three levels above and below the apex of the deformity.

Each of these temporary rods is reduced into the apical bone screw(s) 48 on both sides of the spinal column S. The temporary rods are then reduced gently into the remaining two screws on either side of the apex A. The apical screw(s) are then fully locked and if the apex A is shared between two adjacent levels then both levels are slightly compressed together and strongly partially locked. Very slight gradual compression maneuvers are made on both rods R starting centrally from the apex A. Each screw 48 is then partially locked such that there is no slippage once the compressor is released. A rod manipulator 700 may be used to stabilize the more central screw 48 during each compressive maneuver. Sufficient length may be gained in the rod R to allow the ends to be reduced into the next available screw 48.

If binding or increased resistance is encountered, the most distant screws 48 can be fully locked so as to unload the binding stress on the more central screws 48 to allow further compression. Sequential rounds of apical compression can be continued allowing sufficient time, e.g., a minute, between each round to accommodate soft tissue creep.

Each temporary rod can then be fully locked when the "Smith Peterson Osteotomies" are fully instrumented. At this point, one of the temporary rods can be removed and replaced with a full length substantially hard spinal rod 50 that is contoured to the desired sagittal profile, and will act as the final implanted instrumentation. This permanent spinal rod 50 should be locked completely proximally and at least firmly partially locked distally to maintain the correction while a permanent exchange is made for the second temporary soft rod 50. A brief period of focal periapical compression can be performed before the screws 48 are fully locked. The temporary rod on the other side can be replaced using similar techniques.

In a kyphoscoliosis (T2-L3) presentation of a spinal deformity, the methods presented above for the kyphosis (T2-L3) presentation can be varied as follows to achieve the desired correction. The initial steps described for the kyphosis (T2-L3) presentation can be followed up to the step of sequential compression being completed from the T4 level down to the LIV. At that point, the method steps can be directed to correcting the scoliosis curve of the spinal column. Segments that require correction for scoliosis deformities can be unlocked using an appropriate unlocking instrument for taper lock screws. An example of such an unlocking instrument that is configured to selectively partially lock or fully lock a screw is disclosed in U.S. Patent Application Publication 2008/0093817, the contents of which is hereby fully incorporated by reference. Once unlocked, those screws 48 can be partially locked with the rod reduction device 10 and the partial locker 60 shown in FIGS. 7A and 7B. Beginning proximal to the apex A of the deformity and using the locking instrument, e.g., partial locker 60, on the concave side S1 of the deformity with a denotation extender on the convex side S2, the motion segment can be segmentally axially rotated in the desired alignment. At that point, the locking instrument 60 can be applied to maintain the corrected rotation with the spinal rod 50 on the concave side S1 of the deformity. The derotation extender can then be removed from the screw 48 on the convex side S2 of the segment. Application of compression between the screws 48 on the convex side S2 and a proximal fixation point, e.g., the rod manipulator 700, can be made to level the segment. A locking instrument, e.g., partial locker 60 can then be used to lock the fixation point on the convex side S2 to the rod 50 on the convex side S2.

Derotation/compression may then be repeated sequentially beyond the apex A of the deformity until the desired correction is obtained. The horizontal position of the LIV can be confirmed and the fixation points can be fully locked using a locking instrument. Again, the step of repeating the full locking of all the screws 48 can be done to confirm rigid fixation throughout the construct. As with the other variations of the current method, irrigation, decortication and any needed bone grafting can be accomplished at this time to complete the spinal surgery method.

Figure 8:
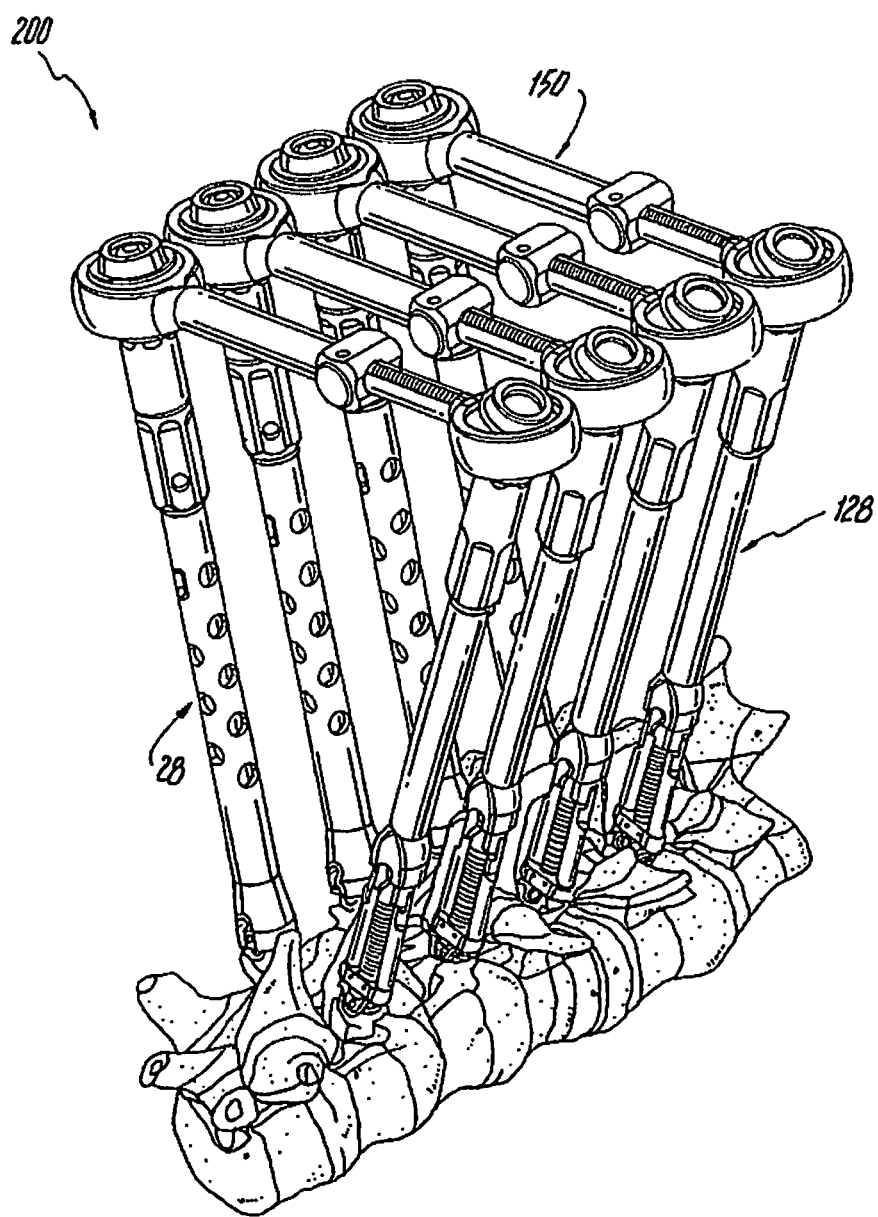
FIG. 8 is a perspective view of a vertebral manipulation system attached to a portion of a spinal column.

Referring now to FIG. 8, a system 200 for repositioning vertebrae is shown. System 200 includes a plurality of manipulators 28, 128 that are coupled to a plurality of rod reduction devices 10 as discussed above with respect to FIG. 3. Manipulators 28, 128, and rod reduction devices 10 are attached to the vertebrae of the spinal column S, as previously discussed. Subsequently, a transverse coupler 150 is attached to a pair of manipulators 28, 128 that are attached to a single vertebral body. Transverse coupler 150 extends transverse to a longitudinal axis of the spinal column S, and in cooperation with the pair of manipulators 28, acts upon a single vertebral body. As shown in FIG. 8, multiple transverse connectors 150 may be coupled to pairs of manipulators 28, 128 with each pair associated with a single vertebral body.

Figure 9A:
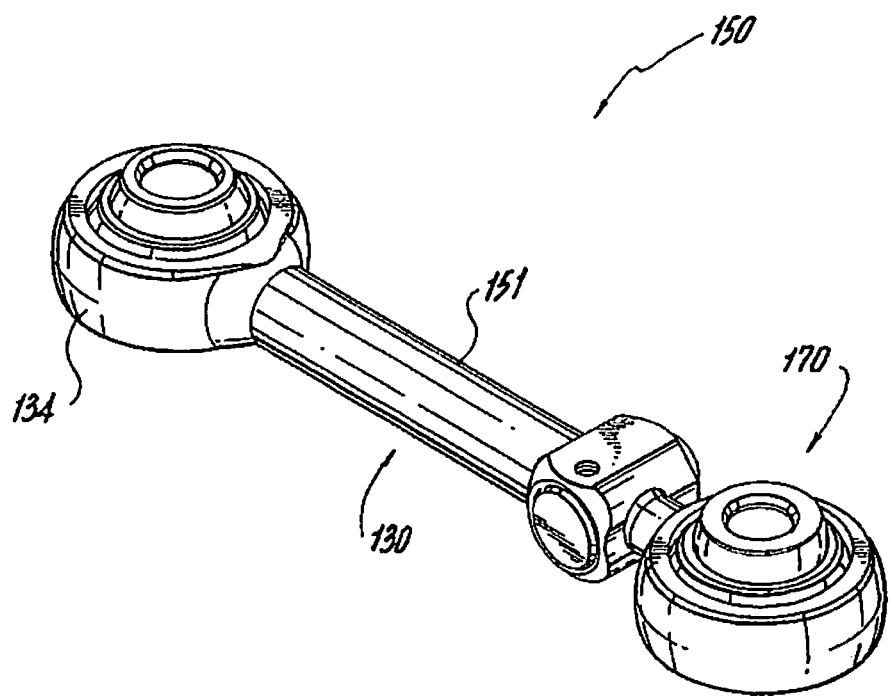
FIG. 9A is a perspective view of a transverse coupler according to an embodiment of the present disclosure.
Figure 9B:
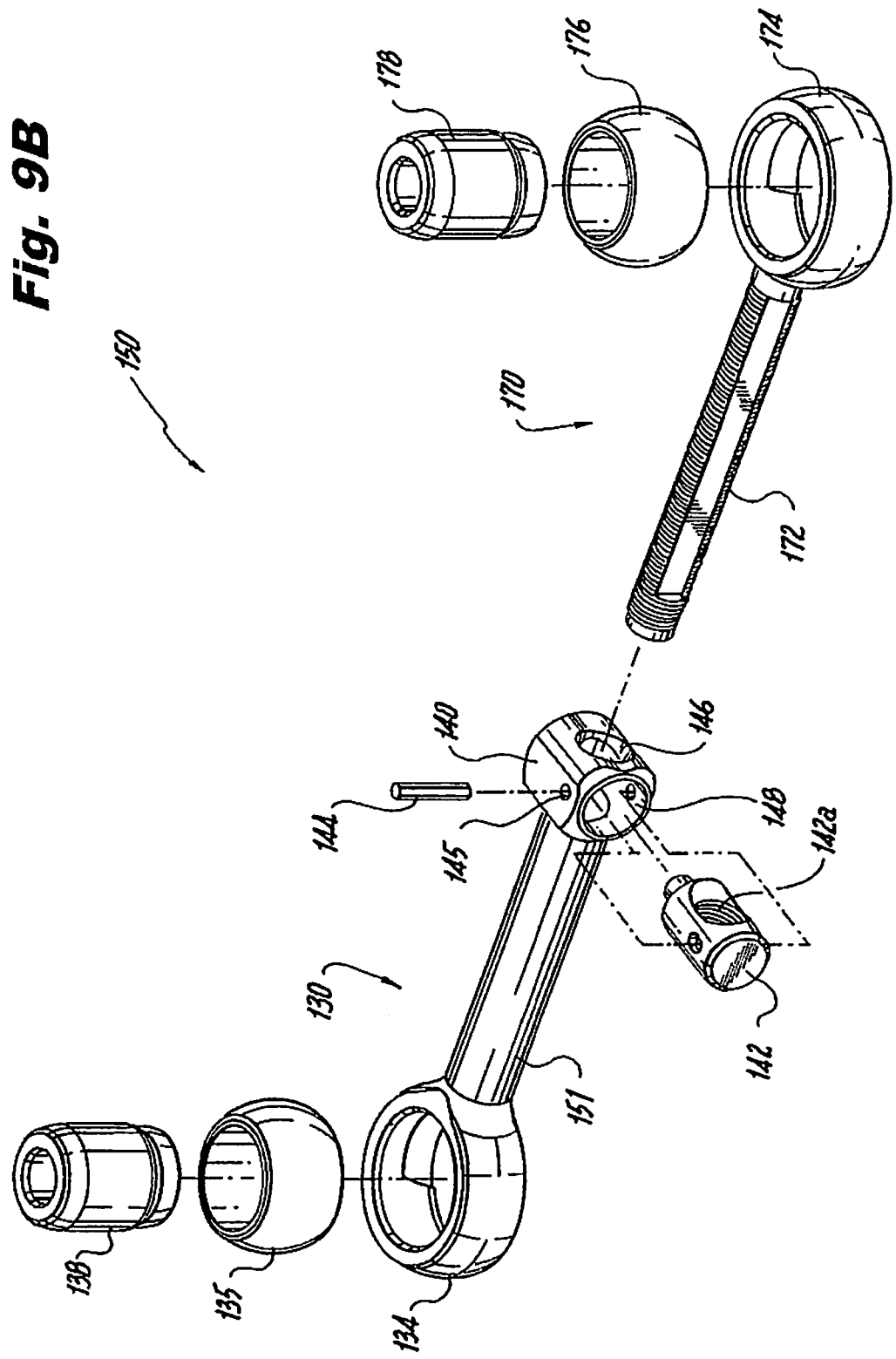
FIG. 9B is an exploded view, with parts separated, of the transverse coupler of FIG. 9A.

Referring now to FIGS. 9A and 9B, transverse coupler 150 includes a first arm portion 130 and a second arm portion 170. First arm portion 130 includes a shaft 151 having a receiver 140 disposed at one end thereof and a ring 134 disposed at the opposing end. A spacer 135 and a sleeve 138 are slidably disposed within ring 134. Sleeve 138 is configured and adapted for releasably receiving a portion of control knobs 32, 132 of the manipulators 28, 128, respectively. Receiver 140 has an opening 146 substantially aligned with shaft 151. An orthogonally oriented hole 148 is also located in receiver 140. A fitting 142 is configured and adapted for insertion into hole 148. Fitting 142 includes a threaded receptacle 142a. After positioning fitting 142 in hole 148, a pin 144 is installed through hole 145 for securing fitting 142 in receiver 140 and is secured in position by friction. The threaded receptacle 142a is aligned with opening 146. Second arm portion 170 includes a threaded shaft 172 that is configured for threadably engaging the threaded receptacle 142a of fitting 142, thereby securing second arm portion 170 with first arm portion 140. In addition, second arm section 170 includes a ring 174, a spacer 176, and a sleeve 178. Spacer 176 and sleeve 178 are slidably disposed within ring 174. Sleeve 178 is configured and adapted for releasably receiving a portion of control knobs 32, 132 of manipulators 28, 128, respectively.

System 200 permits the practitioner to manipulate individual vertebral bodies after the pedicle screws and spinal rods are installed without significantly affecting the adjacent vertebral bodies, thereby providing more precise orientation of the vertebral bodies during a corrective surgical procedure. The practitioner grasps the first arm portion 130 and the second arm portion 170 of the transverse coupler 150 and applies pressure to reposition the vertebral body to the desired position. Alternatively, the practitioner grasps the transverse coupler 150 between the opposing ends of the transverse coupler 150, e.g., the shafts 151, 172, and repositions the vertebral body or bodies.

Figure 10A:
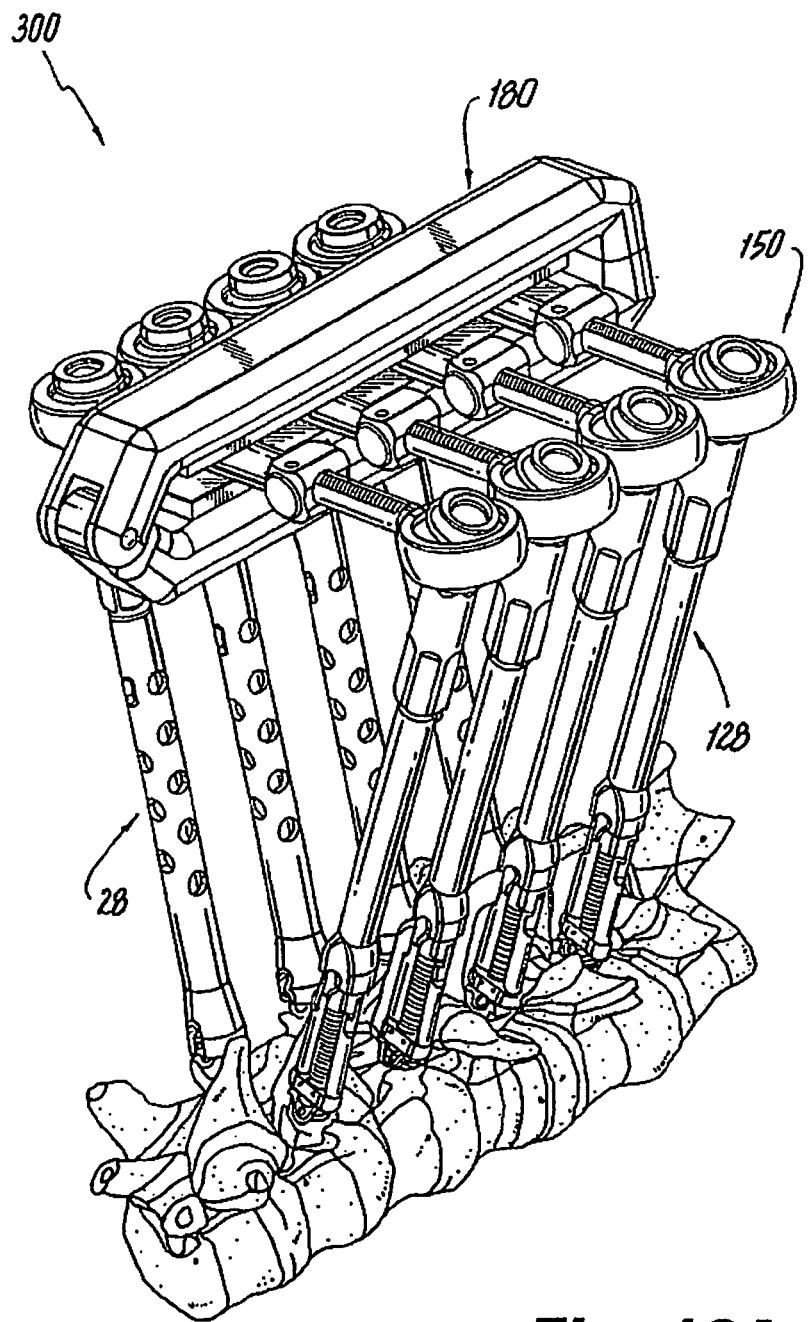
FIG. 10A is a perspective view of a vertebral manipulation system attached to a portion of a spinal column according to another embodiment of the present disclosure.
Figure 10B:
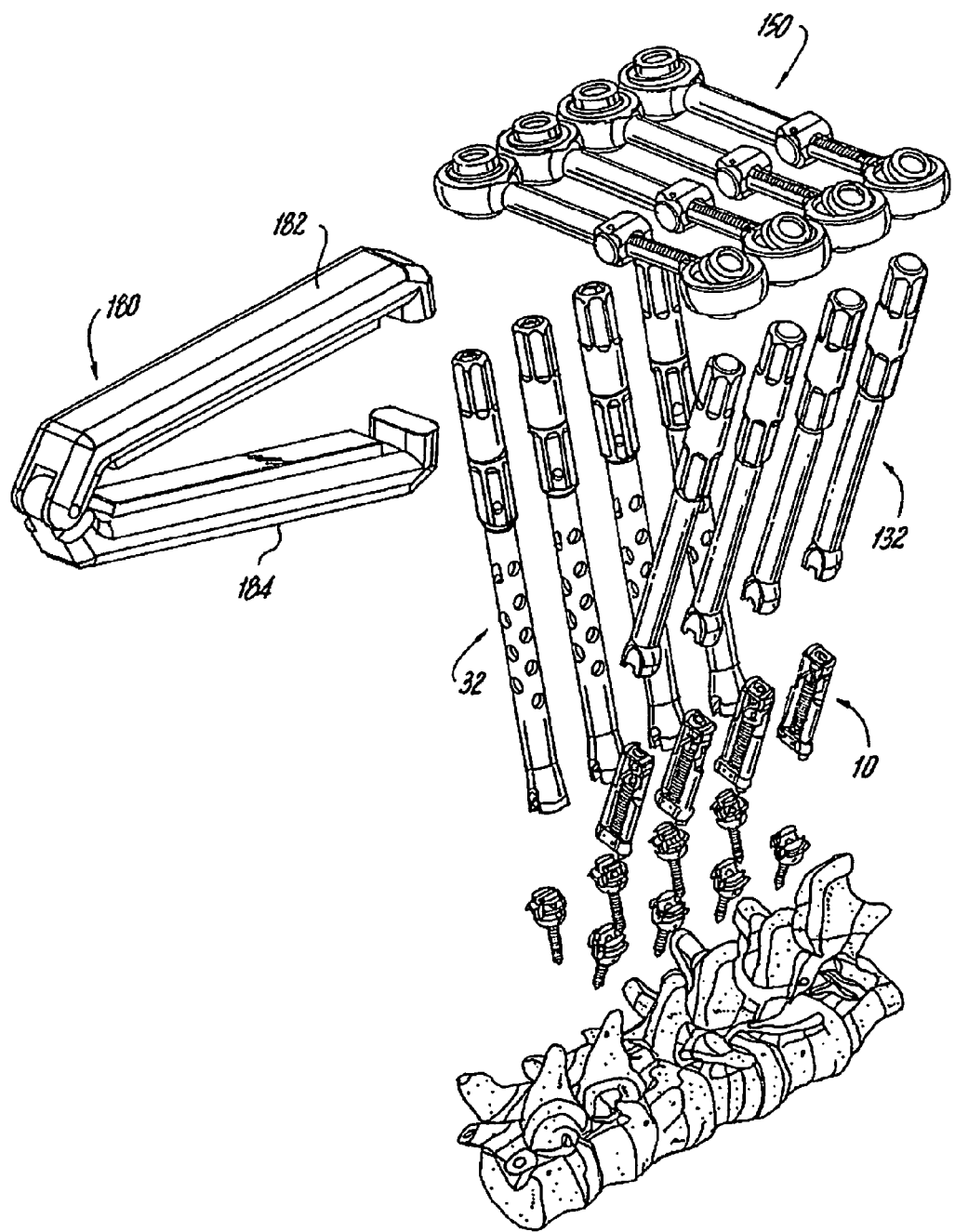
FIG. 10B is an exploded perspective view, with parts separated, of the vertebral manipulation system of FIG. 10A.

Referring now to FIGS. 10A and 10B, a system 300 includes a grip 180. Grip 180 includes a first arm 182 that is pivotably coupled to a second arm 184. When the arms 182, 184 are spaced apart, the arms 182, 184 define a gap therebetween such that the grip 180 may be positioned to capture one or more transverse couplers 150. Once the grip 180 is in a desired position, the arms 182, 184 are pivoted towards each other to close the grip 180 around one or more transverse couplers 150, as seen in FIG. 10A. Although shown attached to multiple transverse couplers 150, it is envisioned that the grip 180 may be used while attached to a single transverse coupler 150. As such, regardless of the number of transverse couplers 150 operatively associated with the grip 180, the practitioner is capable of manipulating the manipulators 28, 128 for repositioning the vertebral body or bodies during performance of the surgical procedure. Further still, the practitioner may remove the grip 180 and reattach it to other transverse couplers 150 as desired for manipulating the selected vertebral bodies in a particular order during performance of the selected procedure.

Figure 11:
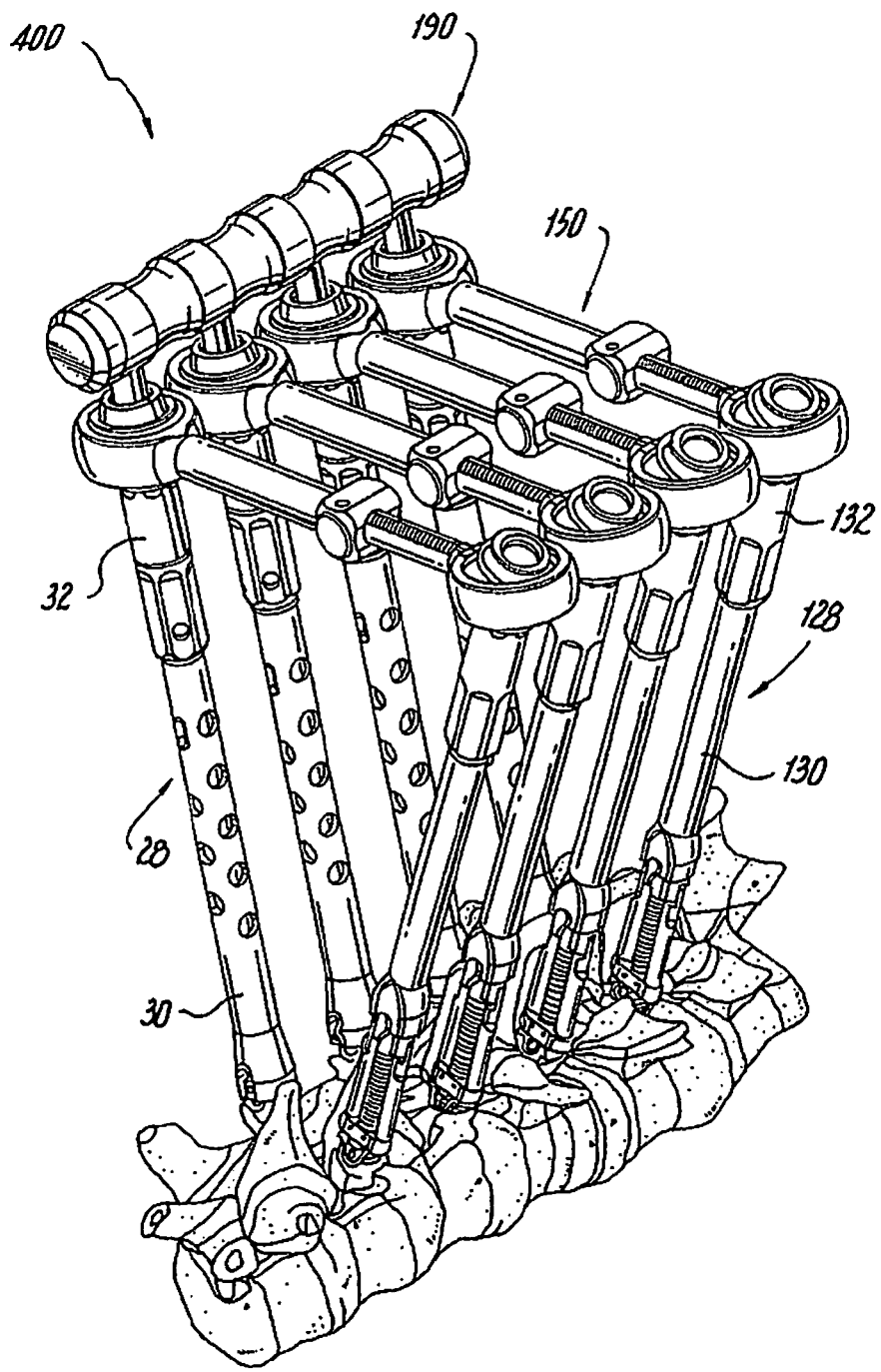
FIG. 11 is a perspective view of a vertebral manipulation system attached to a portion of a spinal column according to a further embodiment of the present disclosure.
Figure 12:
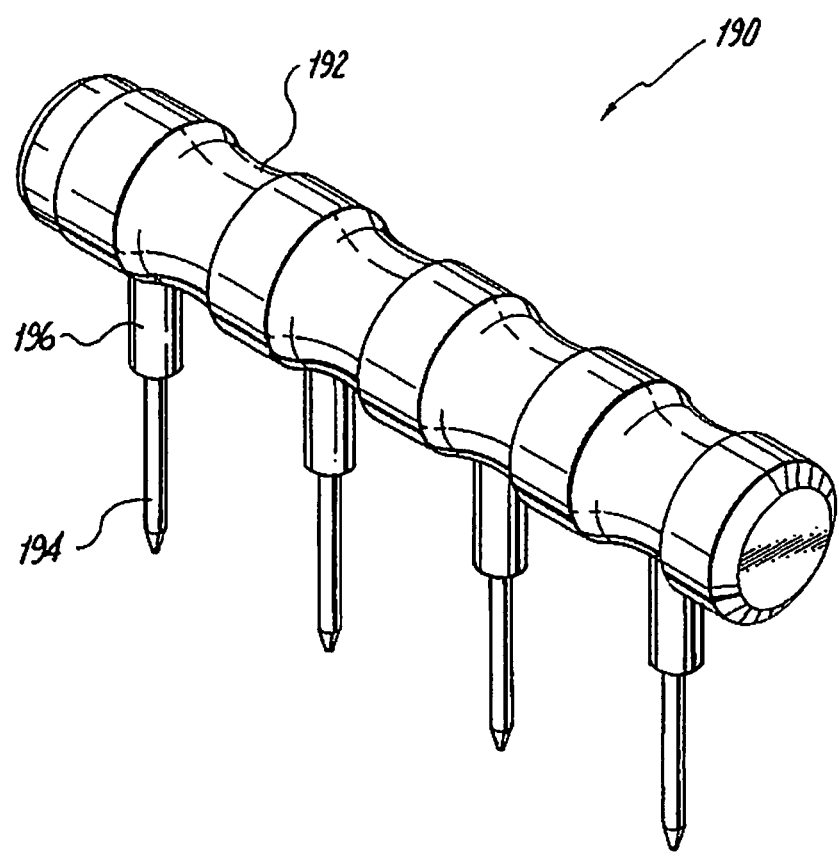
FIG. 12 is a perspective view of a handle.

System 400 will now be described with reference to FIGS. 11 and 12. System 400 is substantially similar to system 200 and 300 with the following exception. The system 400 does not include the grip 180 of system 300. Instead, the system 400 includes a handle 190 including a body 192 including a plurality of rods 194 extending therefrom. A post 196 couples each rod 194 to the body 192. Although the handle 190 is illustrated with four rod 194, it is envisioned that more or fewer rods 194 may be provided with the handle 190. In use, the handle 190 is inserted into one or more manipulators 28, 128 along one side of the vertebral bodies. In this configuration, the system 400 permits manipulation of one or more vertebral bodies only on one side of the longitudinal axis of the spinal column S. As such, the practitioner is able to reposition the selected vertebral bodies by leveraging one side of the spinal column S while leaving the other side unaffected. In this configuration, the movement of handle 190 permits the practitioner to pivot the selected vertebral bodies using their opposing sides as reference points. In the illustrated embodiment of FIG. 11, movement of handle 190 pivots the vertebral bodies through manipulators 28, while manipulators 128 remain relatively stationary and functioning as pivot points. The handle 190 is removable and may be reattached to the opposing side such that the practitioner may incrementally reposition the vertebral bodies. Alternatively, the practitioner may manipulate the handle 190 and reposition the system 400 either medially or laterally to achieve the desired result.

Figure 13:
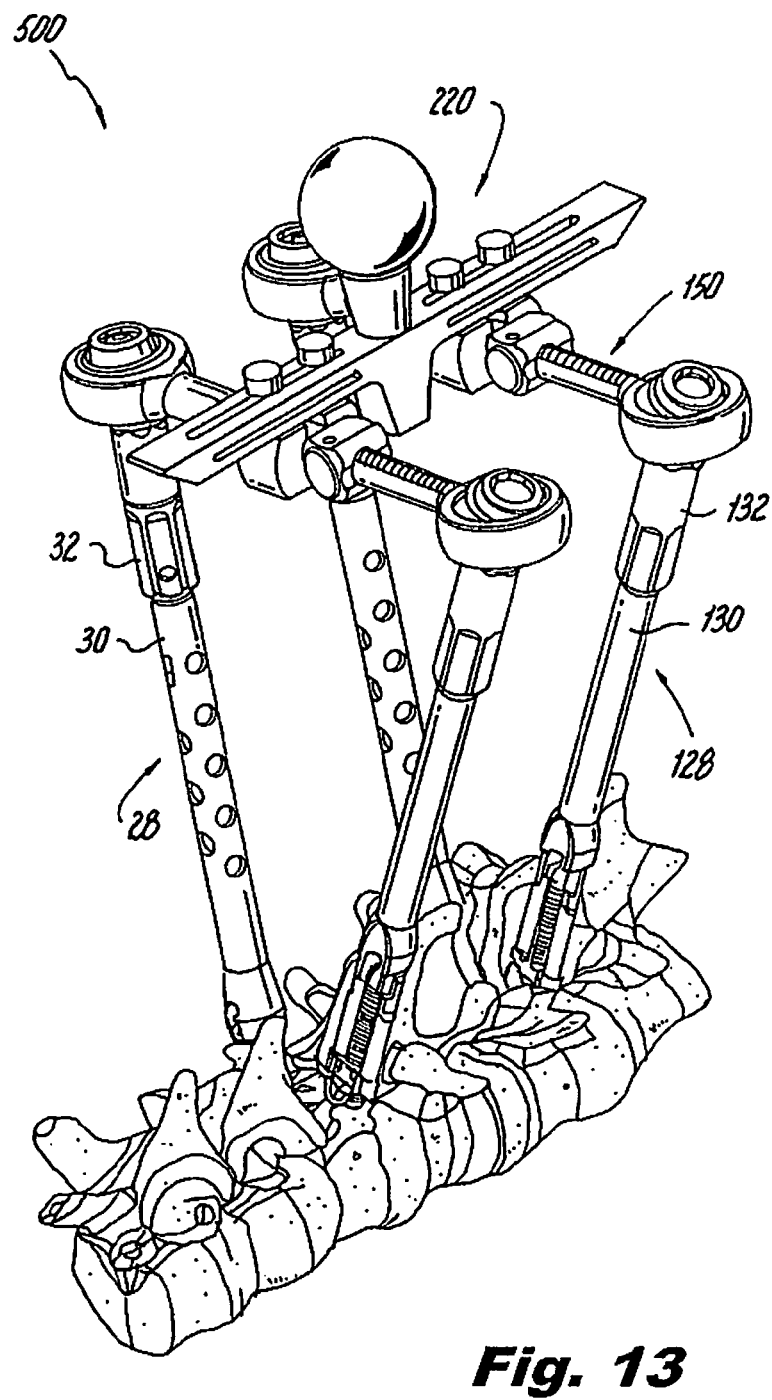
FIG. 13 is a perspective view of a vertebral manipulation system attached to a portion of a spinal column according to an alternate embodiment of the present disclosure.
Figure 14:
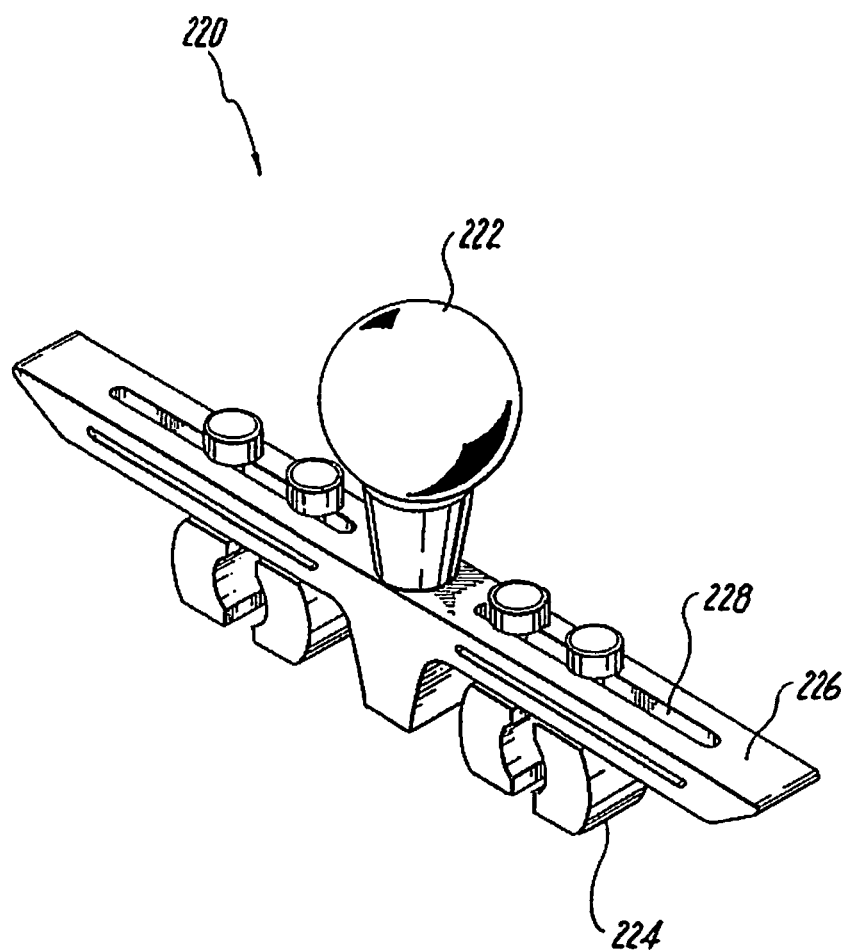
FIG. 14 is a perspective view of an adjustable manipulator.

In a further embodiment of the present disclosure, a system 500 will now be described with reference to FIGS. 13 and 14. The system 500 includes the elements previously discussed with respect to the system 200, however includes a coupler 220. As seen in FIG. 14, the coupler 220 includes a knob 222 disposed along a surface of a bar 226. The bar 226 includes a pair of slots 228. Associated with each slot 228 is a grasper 224 including a pair of spaced apart arcuate members. The graspers 224 are repositionable along the longitudinal axis of the bar 226. Further still, the arms of each grasper 224 are configured to releasably engage either the first arm portion 130 or the second arm portion 170 of the transverse couplers 150. Once connected to a pair of transverse couplers 150, as shown in FIG. 13, repositioning of the vertebral bodies is performed by grasping knob 222 and manipulating the vertebral bodies through the manipulators 28, 128 that are operatively coupled to the transverse couplers 150. Alternately, the practitioner may grab one or both sections of the bar 226 for manipulating the vertebral bodies. In use, system 500 facilitates manipulation of the vertebral bodies in a multitude of orientations facilitating improved flexibility in performing the selected procedure.

It is noted that any system including a first rod reduction device coupled to a first vertebral body of a spinal column, a second rod reduction device coupled to a second vertebral body of a spinal column, a first manipulator coupled to the first rod reduction device, a second manipulator coupled to the second rod reduction device, and a coupler coupling the first and second manipulators is within the scope of the present disclosure. In an embodiment, the system may include a first and second rod reduction devices coupled to a first vertebral body of a spinal column, wherein a first manipulator is coupled to the first rod reduction device and a second manipulator is coupled to the second rod reduction device, a second assembly including a third rod reduction device and a fourth rod reduction device, the third and fourth rod reduction devices coupled to a second vertebral body of the spinal column, wherein a third manipulator is coupled to the third rod reduction device and a fourth manipulator is coupled to the fourth reduction device, and a coupler coupling the first and second assemblies.

It is within the scope of the present disclosure to provide a kit for use with the method disclosed herein. The kit includes at least two polyaxial bone screws, at least two uniplanar bone screws, at least two monoaxial bone screws, and at least two spinal rods, as well as associated tools for using the bone screws to connect the surgical rods to the adjacent spinal vertebrae. In addition, the kit can contain surgical rods, such as for example, connecting rods. Additional devices such as cross-connectors or links can also be included in the kit.

It will be understood by those skilled in the art that various modifications and changes in form and detail may be made therein without departing from the scope and spirit of the present disclosure. Accordingly, modifications such as those suggested above, but not limited thereto, are to be considered within the scope of the disclosure. Therefore, the above description should not be construed as limited to the disclosed embodiments. Other embodiments within the scope and spirit of the present invention will appear to those skilled in the art. For example, while the rod reduction device 10 is one device for use in the methods disclosed herein, it is envisioned that alternative devices that are capable of grasping a bone screw head and facilitating reduction of a rod into a recess of a bone screw may be used instead and in substantially the same way described. It is also contemplated, for example, that the rod reduction devices could be adapted to mount to and work with setscrew style bone screws and that uniplanar and monoaxial setscrew style bone screws, the setscrew would be insertable through the rod reduction device. It is also envisioned any elongated tool capable of connecting to the head of a bone screw and forcing a spinal rod into position within that bone screw receiving slot would be suitable for the manipulator described herein.

What is claimed is:

1. A method for correcting a deformity of a spinal column comprising:
    implanting a plurality of bone screws into a plurality of vertebrae of a spinal column;
    mounting rod reduction jacks to at least some of the plurality of bone screws;
    inserting a spinal rod between the rod reduction jacks and the bone screws;
    partially actuating the rod reduction jacks to gradually reduce the spinal rod to each bone screw while effecting realignment of the vertebrae relative to one another;
    removing the rod reduction jacks from a first side of the spinal column;
    repeating the above steps on a second side of the spinal column; and
    with the spinal rods partially locked in the bone screws, facilitating sagittal alignment of the spinal rods, wherein one portion of each of the rods is anchored to vertebrae, including a lowest instrumented vertebra, using polyaxial screws and the remaining portion of each of the rods is anchored to the vertebrae using uniplanar taper lock bone screws with the lowest instrumented vertebra anchored to the rods using monoaxial bone screws.

2. The method of claim 1, wherein the rod reduction jacks are applied to the bone screws bilaterally to both sides of the spinal column.

3. The method of claim 1, wherein counter-torsion of a lowest instrumented vertebra is accomplished.

4. The method of claim 1, wherein partial actuation of the rod reduction jacks to each bone screw is achieved by mounting a partial screw locking instrument over a single rod reduction jack of the rod reduction jacks and a corresponding bone screw of the bone screws and partially locking the corresponding bone screw with the single rod reduction jack in place.

5. The method of claim 1, further comprising:
    manually manipulating the spinal column to effect realignment of the vertebrae relative to each other; and
    fully reducing the spinal rod to each bone screw subsequent to the manual manipulation of the spinal column.

6. The method of claim 1, wherein alignment tubes are mounted over one or more of the rod reduction jacks.

7. The method of claim 1, wherein the rods are pre-bent in a physiological sagittal plane prior to attachment.

8. The method of claim 1, wherein taper lock screws are used in one portion of the spinal construct and set screw or nut style screws are used in another portion of the spinal construct.

9. A method for correcting a deformity of a spinal column comprising:
    implanting a plurality of bone screws into a plurality of vertebrae of a spinal column;
    mounting rod reduction jacks to at least some of the plurality of bone screws;
    inserting a spinal rod between the rod reduction jacks and the bone screws;
    partially actuating the rod reduction jacks to gradually reduce the spinal rod to each bone screw while effecting realignment of the vertebrae relative to one another;
    removing the rod reduction jacks from a first side of the spinal column;
    repeating the above steps on a second side of the spinal column; and
    with the spinal rods partially locked in the bone screws, facilitating sagittal alignment of the spinal rods, wherein taper lock screws are used in one portion of the spinal construct and set screw or nut style screws are used in another portion of the spinal construct.

10. The method of claim 9, wherein the rod reduction jacks are applied to the bone screws bilaterally to both sides of the spinal column.

11. The method of claim 9, wherein counter-torsion of a lowest instrumented vertebra is accomplished.

12. The method of claim 9, wherein partial actuation of the rod reduction jacks to each bone screw is achieved by mounting a partial screw locking instrument over a single rod reduction jack of the rod reduction jacks and a corresponding bone screw of the bone screws and partially locking the corresponding bone screw with the single rod reduction jack in place.

13. The method of claim 9, further comprising:
    manually manipulating the spinal column to effect realignment of the vertebrae relative to each other; and
    fully reducing the spinal rod to each bone screw subsequent to the manual manipulation of the spinal column.

14. The method of claim 9, wherein alignment tubes are mounted over one or more of the rod reduction jacks.

15. The method of claim 9, wherein the rods are pre-bent in a physiological sagittal plane prior to attachment.

16. The method of claim 9, wherein uniplanar taper lock screws are used in one portion of the spinal construct and polyaxial screws are used in another portion of the spinal construct.

* * * * *